United States Patent
Kim et al.

(10) Patent No.: US 10,688,135 B2
(45) Date of Patent: Jun. 23, 2020

(54) COMPOSITION FOR TREATING ISCHEMIC DISEASES OR NEUROINFLAMMATORY DISEASES, COMPRISING SECRETOME OF NEURAL PRECURSOR CELLS AS ACTIVE INGREDIENT

(71) Applicant: S-BIOMEDICS, Seoul (KR)

(72) Inventors: Dong Wook Kim, Seoul (KR); Han Soo Kim, Goyang-si (KR)

(73) Assignee: S-BIOMEDICS, Seoul (KR)

( * ) Notice: Subject to any disclaimer, the term of this patent is extended or adjusted under 35 U.S.C. 154(b) by 0 days.

(21) Appl. No.: 15/739,958

(22) PCT Filed: Jun. 27, 2016

(86) PCT No.: PCT/KR2016/006848
§ 371 (c)(1),
(2) Date: Dec. 26, 2017

(87) PCT Pub. No.: WO2016/209057
PCT Pub. Date: Dec. 29, 2016

(65) Prior Publication Data
US 2018/0228845 A1 Aug. 16, 2018

(30) Foreign Application Priority Data

Jun. 26, 2015 (KR) .................. 10-2015-0091378

(51) Int. Cl.
| | |
|---|---|
| A61K 35/30 | (2015.01) |
| A61K 35/12 | (2015.01) |
| A61P 9/10 | (2006.01) |
| A61P 25/00 | (2006.01) |
| A61K 38/17 | (2006.01) |
| A61K 9/00 | (2006.01) |
| A61K 47/36 | (2006.01) |
| A61P 29/00 | (2006.01) |
| A61K 38/19 | (2006.01) |
| A61K 9/10 | (2006.01) |
| A61K 39/395 | (2006.01) |

(52) U.S. Cl.
CPC ............ *A61K 35/30* (2013.01); *A61K 9/00* (2013.01); *A61K 9/10* (2013.01); *A61K 35/12* (2013.01); *A61K 38/17* (2013.01); *A61K 38/19* (2013.01); *A61K 39/395* (2013.01); *A61K 47/36* (2013.01); *A61P 9/10* (2018.01); *A61P 25/00* (2018.01); *A61P 29/00* (2018.01)

(58) Field of Classification Search
CPC ..... A61K 2300/00; A61K 35/12; A61P 25/00; A61P 9/10
See application file for complete search history.

(56) References Cited

U.S. PATENT DOCUMENTS

2007/0020247 A1  1/2007  Ravindran et al.
2017/0136068 A1  5/2017  Kim et al.

FOREIGN PATENT DOCUMENTS

| KR | 20130116552 A | 10/2013 |
| KR | 20140071512 A | 6/2014 |
| WO | WO-2015/199499 A1 | 12/2015 |

OTHER PUBLICATIONS

Chang et al., Cell Transplant, 22(8):1427-40 (Year: 2013).*
Barral et al., Stem Cell Research, 10(2):133-46 (Year: 2013).*
Ranganath et al., Cell Stem Cell 10, Mar. 2, 2012 (Year: 2012).*
Drago et al., Biochimie, 95: 2271-2285, 2013 (Year: 2013).*
Examination Report dated May 25, 2018 for European Patent Application No. 16814770.0, Kim et al., "Composition for treating ischemic diseases or neurogenic inflammatory disorders, containing secretome of neural progenitor cells as active ingredient," filed Jun. 27, 2016 (7 pages).
Teixeira et al., "Secretome of mesenchymal progenitors from the umbilical cord acts as modulator of neural/glial proliferation and differentiation," Stem Cell Rev and Rep. 11(2):288-97 (2015).
Chang et al., "Therapeutic potential of human induced pluripotent stem cells in experimental stroke," Cell Transplant. 22(8):1427-40 (2013).
Drago et al., "The stem cell secretome and its role in brain repair," Biochimie. 95(12):2271-85 (2013).
Laterza et al., "iPSC-derived neural precursors exert a neuroprotective role in immune-mediated demyelination via the secretion of LIF," Nat Commun. 4:1-16 (2013).
Li et al., "Prosaposin in the secretome of marrow stroma-derived neural progenitor cells protects neural cells from apoptotic death," J Neurochem. 112(6):1527-38 (2010).
Office Action dated Oct. 30, 2018 for Japanese Patent Application No. 2017-566411, Kim et al., "Composition for Treating Ischemic Diseases or Neurogenic Inflammatory Disorders, Containing Secretome of Neural Progenitor Cells as Active Ingredient," filed Jun. 27, 2016 (6 pages).
Kim et al., "Highly Pure and Expandable PSA-NCAM-Positive Neural Precursors from Human ESC and iPSC-Derived Neural Rosettes," PLoS One. 7(7):e39715 (12 pages) (2012).
Kim et al., "PSA-NCAM+ Neural Precursor Cells from Human Embryonic Stem Cells Promote Neural Tissue Integrity and Behavioral Performance in a Rat Stroke Model," Stem Cell Rev. 10(6):761-71 (2014).
Lee et al., "PSA-NCAM-Negative Neural Crest Cells Emerging during Neural Induction of Pluripotent Stem Cells Cause Mesodermal Tumors and Unwanted Grafts," Stem Cell Reports. 4(5):821-34 (2015).

(Continued)

*Primary Examiner* — Kimberly Ballard
*Assistant Examiner* — Stacey N MacFarlane
(74) *Attorney, Agent, or Firm* — Clark & Elbing LLP; Susan M. Michaud

(57) ABSTRACT

The present invention provides a composition for treating ischemic diseases or neuroinflammatory disorders, comprising a secretome of neural precursor cells (NPCs) as an active ingredient. The secretome of NPCs, of the present invention, reduces an ischemic injury site and enables neurological functions to recover by means of roles such as anti-inflammation, neovascularization regeneration, and activation and proliferation of inherent stem cells, thereby being usable as a therapeutic agent for ischemic diseases and degenerative nervous system disorders such as nerve damage diseases caused by inflammation. Particularly, the secretome of NPCs, of the present invention, has an excellent behavior improvement effect when administered multiple times.

11 Claims, 22 Drawing Sheets

(56) References Cited

OTHER PUBLICATIONS

English Translation of International Search Report and Written Opinion of the International Searching Authority dated Dec. 8, 2016 for International Patent Application No. PCT/KR2016/006848, Kim et al., "Composition for Treating Ischemic Diseases or Neurogenic Inflammatory Disorders, Containing Secretome of Neural Progenitor Cells As Active Ingredient," filed Jun. 27, 2016 (10 pages).

Cunningham et al., "Secreted phospholipase A2 activity in experimental autoimmune encephalomyelitis and multiple sclerosis," J Neuroinflammation. 3:26 (2006) (8 pages).

Doorn et al., "Microglial phenotypes and toll-like receptor 2 in the substantia nigra and hippocampus of incidental Lewy body disease cases and Parkinson's disease patients," Acta Neuropathol Commun. 2:90 (2014) (17 pages).

Millington et al., "Chronic neuroinflammation in Alzheimer's disease: new perspectives on animal models and promising candidate drugs," Biomed Res Int. Article ID 309129 (2014) (10 pages).

Philips et al., "Glial cells in Amyotrophic Lateral Sclerosis," available in PMC Dec. 1, 2015, published in final edited form as: Exp. Neurol. 262PB: 111-120, 2014. doi:10.1016/j.expneurol.2014.05.015, (2014) (22 pages).

\* cited by examiner

COMPOSITION FOR TREATING ISCHEMIC DISEASES OR NEUROINFLAMMATORY DISEASES, COMPRISING SECRETOME OF NEURAL PRECURSOR CELLS AS ACTIVE INGREDIENT

TECHNICAL FIELD

The present invention relates to a composition comprising the secretome of neural precursor cells (NPC) as an active ingredient for treating ischemic diseases or neuroinflammatory diseases.

BACKGROUND ART

Stem cells are regarded as a promising therapeutic candidate material for various diseases due to the multipotency thereof. For example, mesenchymal stem cells (MSCs) release many nutritional factors that can be easily obtained and isolated and achieve the promotion of angiogenesis and the inhibition of inflammation (Non-patent literature 1). These characteristics of MSCs have been considered in studies for the application to the treatment of a number of human diseases. Recent studies have found that MSCs contribute to the tissue repair in a large number of animal models and human clinical treatments (Non-patent literatures 2, 3). Several reports stated the in vitro differentiation ability of MSC into the neural lineage (Non-patent literature 4) and astrocytes (Non-patent literature 3), but there is no definite evidence as to what functions the differentiated cells perform in vivo. It seems that the favorable effect of MSCs is induced by paracrine mechanisms rather than cell replacement, and therefore, the transplantation of MSCs would have temporary and limited effects but not the alleviation maintained for a long period of time (Non-patent literature 5).

In contrast, embryonic stem cells (ESCs) can differentiate into cell types derived from all three embryonic germ layers, and have a strong self-renewal ability. Noticeably, neural precursor cells (NPCs) derived from ESCs, first, differentiate into a particular cell type of neural lineage cells including neural cells, astrocytes, and oligodendrocyte, and thus are considered to be an ideal cell source for repair or regeneration of damaged brain tissues. These cells secrete certain factors for promoting the survival and proliferation of endogenous neural precursor cells (Non-patent literature 6). However, it has not yet been known how NPCs differentiated from ESCs or the conditioned medium of NPCs contribute to the improvement of functions after administration into disease models Reprogrammed stem cells refer to cells reprogrammed to acquire pluripotency by subjecting somatic cells to an artificial reprogramming procedure through various means, such as gene transduction/transcriptional factor induction, chemical treatment and growth factor treatment. The reprogrammed stem cells are called induced pluripotent stem cells (iPSCs) (non-patent document 7). When compared with embryonic stem cells, these cells show very high similarity in view of cell morphology, culture condition, proliferation rate, gene expression profile, chromosomal alteration patterns, pluripotency, and teratoma forming ability in immunodeficient mice. The differentiation potency of the induced pluripotent stem cells is similar to that of embryonic stem cells, but it is not well known how NPCs differentiated therefrom or an NPC conditioned medium contributes to the improvement of functions after administration into disease models.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are explained more clearly.

PRIOR ART

Non-Patent Literature

1. Caplan, A. I., & Dennis, J. E. (2006). Mesenchymal stem cells as trophic mediators. *Journal of Cellular Biochemistry*, 98, 1076-1084.
2. Chen, J., Li, Y., Katakowski, M., et al. (2003). Intravenous bone marrow stromal cell therapy reduces apoptosis and promotes endogenous cell proliferation after stroke in female rat. *Journal of Neuroscience Research*, 73, 778-786.
3. Kopen, G. C., Prockop, D. J., & Phinney, D. G. (1999). Marrow stromal cells migrate throughout forebrain and cerebellum, and they differentiate into astrocytes after injection into neonatal mouse brains. *Proceedings of the National Academy of Sciences*, 96, 10711-10716.
4. Bae, K. S., Park, J. B., Kim, H. S., Kim, D. S., Park, D. J., & Kang, S. J. (2011). Neuron-like differentiation of bone marrowderived mesenchymal stem cells. *Yonsei Medical Journal*, 52,401-412.
5. Cho, S. R., Kim, Y. R., Kang, H. S., et al. (2009). Functional recovery after the transplantation of neurally differentiated mesenchymal stem cells derived from bone barrow in a rat model Functional recovery after the transplantation of spinal cord injury. *Cell Transplantion*, 18, 1359-1368.
6. Capone, C., Frigerio, S., Fumagalli, S., et al. (2007). Neurosphere-derived cells exert a neuroprotective action by changing the ischemic microenvironment. *PLoS One*, 7, e373.
7. Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. *Cell* 131: 861-872.

DETAILED DESCRIPTION OF THE INVENTION

Technical Problem

The present inventors have researched and endeavored to develop a fundamental treatment method for ischemic diseases and neuroinflammatory diseases. As a result, the present inventors have confirmed that as a different approach from stem cell transplantation, the administration of the neural precursor cell (NPC) secretome (i.e., conditioned medium from NPC) into a lesion site reduces the extent of cerebral ischemic infarction and restores neural functions, thereby effectively treating ischemic diseases, neurological damage diseases, and degenerative nervous system diseases, and thus, the present inventors have completed the present invention.

Accordingly, an aspect of the present invention is to provide a composition for treating cerebral ischemic diseases or neuroinflammatory diseases.

Another aspect of the present invention is to provide a method for preventing or treating cerebral ischemic diseases or neuroinflammatory diseases.

Other purposes and advantages of the present disclosure will become more obvious with the following detailed description of the invention, claims, and drawings.

Technical Solution

In accordance with an aspect of the present invention, there is provided a composition for treating cerebral ischemic diseases or neuroinflammatory diseases, the composition comprising a secretome of neural precursor cells (NPCs) as an active ingredient.

The present inventors have studied and endeavored to develop a fundamental treatment method for cerebral ischemic diseases and neuroinflammatory diseases. As a result, the present inventors have confirmed that as a different approach from stem cell transplantation, the administration of the neural precursor cell (NPC) secretome into a lesion site reduces an area of ischemic injury and restores neural functions, thereby effectively treating cerebral ischemic diseases, neurological damage diseases, and degenerative nervous system diseases.

As used herein, the term "secretome of neural precursor cells" refers to the totality (or collection) of proteins secreted from neural precursor cells to the surroundings of cells (into culture medium) when the neural precursor cells are cultured.

According to an embodiment of the present invention, the neural precursor cells used in the preparation of the secretome of the present invention are the neural precursor cells differentiated from pluripotent stem cells.

As used herein, the term "stem cells" is a generic term for undifferentiated cells before differentiation into respective cells constituting tissues, and the stem cells have an ability to differentiate into particular cells by particular differentiation stimulations (environment). Unlike terminally differentiated, non-proliferating, cells, the stem cells are capable of producing identical cells to the original stem cells through cell division (self-renewal), and have plasticity in differentiation, in which the stem cells are able to differentiate into particular cells by the application of the differentiation stimulation and may be differentiated into various cells under different environments or by differentiation stimuli.

The stem cells used in the present invention are pluripotent stem cells that proliferate indefinitely in vitro and can be differentiated into various cells derived from all embryonic layers (ectoderm, mesoderm, and endoderm). More specifically, the pluripotent stem cells are embryonic stem cells, induced pluripotent stem cells (iPSCs), embryonic germ cells, or embryonic carcinoma cells.

The embryonic stem cells are derived from the inner cell mass (ICM) of the blastocyst, and the embryonic germ cells are derived from primordial germ cells present in 5-10 week-old gonadal ridges.

Induced pluripotent stem cells (iPSCs) are one type of pluripotent stem cells artificially derived from non-pluripotent cells (e.g., somatic cells) by transducing particular genes conferring pluripotency therein. Induced pluripotent stem cells are considered to be the same as pluripotent stem cells (e.g., embryonic stem cells) since the induced pluripotent stem cells have highly similar stem cell genes and protein expression, chromosomal methylation pattern, doubling time, embryoid body formation capacity, teratoma formation capacity, viable chimera formation capacity, hybrid formation, and differentiation ability as embryonic stem cells.

According to an embodiment of the present invention, the neural precursor cells (NPCs) are neural precursor cells before or after a stage of neural rosettes formed by inducing the differentiation of pluripotent stem cells (e.g., embryonic stem cells or induced pluripotent stem cells) into neural lineage cells.

According to an embodiment of the present invention, the neural precursor cells are poly-sialylated neural cell adhesion molecule (PSA-NCAM)-positive neural precursor cells (NPCs).

According to another embodiment of the present invention, the neural precursor cells are poly-sialylated neural cell adhesion molecule (PSA-NCAM)-negative neural precursor cells (NPCs).

The PSA-NCAM-positive or negative neural precursor cells may be purified from neural rosettes, which are differentiated from pluripotent stem cells through the stimulation of neural differentiation, using an anti-PSA-NCAM-antibody. The term "neural rosettes" refers to neural stems cell at the initial stage in the neural differentiation procedure of human embryonic stem cells, and the neural rosette has a cylindrical radial form. The neural rosettes are composed of cells expressing initial neuroectodermal markers, such as Pax6 and Sox1, and may be differentiated into various neural cells and neuroglial cells.

The stimulation of neural differentiation may be induced by a method that is ordinarily conducted in the art, for example, serum-free media (Tropepe V et al., Neuron. 30:6578 (2001)), fibroblast growth factors (FGFs), and treatment with morphogens, such as Wnt and retinoic acid (RA) (Ying Q L et al. Nat Biotechnol. 21:183186 (2003)), but is not limited thereto.

Polyclonal antibodies or monoclonal antibodies may be used as the antibody-mediated cell purification. The antibodies against PSA-NCAM may be produced by the methods that are conventionally conducted in the art, for example, a fusion method (Kohler and Milstein, European Journal of Immunology, 6:511-519 (1976)), a recombinant DNA method (U.S. Pat. No. 4,816,56), or a phage antibody library method (Clackson et al, Nature, 352:624-628 (1991) and Marks et al, J. Mol. Biol., 222:58, 1-597 (1991)). A general procedure for antibody production is described in detail in Harlow, E. and Lane, D., Using Antibodies: A Laboratory Manual, Cold Spring Harbor Press, New York, 1999; Zola, H., Monoclonal Antibodies: A Manual of Techniques, CRC Press, Inc., Boca Raton, Fla., 1984; and Coligan, CURRENT PROTOCOLS IN IMMUNOLOGY, Wiley/Greene, N.Y., 1991, the disclosure of which are incorporated herein by reference. For example, hybridoma cells producing monoclonal antibodies may be obtained by fusing immortal cell lines to antibody-producing lymphocytes, the technology for which has been well known to those skilled in the art, and can be easily conducted. The polyclonal antibodies may be obtained by injecting PSA-NCAM antigens into an appropriate animal, collecting antisera from the animal, and then isolating antibodies from the antisera using the known affinity technique.

As used herein to recite the PSA-NCAM, the term "antibody" refers to an antibody specific to PSA-NCAM, and the antibody specifically binds to the PSA-NCAM protein, and includes a complete form of an antibody and an antigen binding fragment of the antibody molecule. The complete antibody has a structure having two full-length light chains and two full-length heavy chains, and the light chains are linked to the heavy chains via a disulfide linkage, respectively. The antigen-binding fragment of the antibody molecule is a fragment having an antigen binding function, and includes Fab, F(ab'), F(ab')2, and Fv.

For the separation of PSA-NCAM-positive neural precursor cells using an antibody, fluorescence-activating cell sorters (FACS), magnetic activated cell sorter (MACS), antibody-coated plastic adherence, and complement-mediated lysis may be used.

According to an embodiment, the secretome is in a form of being contained in a cell conditioned medium obtained by culturing neural precursor cells in an animal cell culture medium. That is, the composition of the present invention may be contained in a cell conditioned medium of neural precursor cells, containing a secretome of neural precursor cells.

According to an embodiment of the present invention, the cell conditioned medium of the neural precursor cells may be obtained by culturing the neural precursor cells in a serum-free cell culture medium containing insulin/transferrin/selenium (ITS) and basic fibroblast growth factor (bFGF) and then removing the cells. For the culturing, neural precursor cells that are obtained by subculturing (e.g., at least four passages) the neural precursor cells in a bFGF-containing animal cell culture medium supplemented with, for example, N2, B-27, and/or Gem21.

The removal of the cells from the conditioned medium may be conducted by using an ordinary cell separation method, such as centrifugation or filtration.

For the animal cell culture medium, an ordinary medium that is used for culturing neural precursor cells may be used without limitation. For example, DMEM/F12 may be used.

According to an embodiment of the present invention, the neural precursor cells are differentiated from human induced pluripotent stem cells (iPSCs), and the secretome of neural precursor cells include the following proteins:

Agrin, annexin A5, BSG (Basigin), biglycan, calponin-3, coactosin-like protein, cofilin-1, collagen alpha-2, cullin-3, destrin, dystroglycan, ephrin-B2, exportin-2, ezrin, fibronectin, fibulin-1, frizzled-related protein, gelatin-3 binding protein, granulins, growth/differentiation factor 11, haptoglobin, hemopexin, high mobility group protein B2, hornerin, importin-9, insulin-like growth factor-binding protein 2, Lupus La protein, macrophage migration inhibitory factor, midkine, moesin, neuropilin 2, pleiotrophin, profilin-1, protein DJ-1, radixin, secreted frizzled-related protein-2, septin-11, talin-1, testican, thymopoietin, transgelin-3 and vimentin.

According to an embodiment of the present invention, the neural precursor cells are differentiated from human embryonic stem cells (ESCs), and the secretome of neural precursor cells include the following proteins:

Agrin, annexin A2, attractin, biglycan, ceruloplasmin, cofilin-1, collagen alpha-1, coronin-1X, dermicidin, DERP12, eprin-B3, exostosin-2, ezrin, gelatin-3 binding protein, granulins, growth/differentiation factor 11, haptoglobin, hemopexin, high mobility group protein B2, hornerin, insulin-like growth factor-binding protein 2, Lupus La protein, midkine, moesin, multiple epidermal growth factor-like domains protein 8, nidogen-1, parathymosin, profilin-2, protein DJ-1, secreted frizzled-related protein-2, secretogranin, talin-1, thymosin beta-4, TGFBI (Transforming growth factor-beta-induced protein ig-h3), transgelin and vimentin.

As used herein, the term "treatment" refers to: (a) suppressing the progression of disease, disorder, or symptom; (b) reducing disease, disorder, or symptom; or (c) curing the disease, disorder, or symptom. The composition of the present invention suppresses the development of symptoms of cerebral ischemic disease or neuroinflammatory disease, or removes or reduces the symptoms of cerebral ischemic disease or neuroinflammatory disease. Therefore, the composition of the present invention per se may be a composition for treating cerebral ischemic disease or neuroinflammatory disease, or may be applied as a treatment adjuvant for the diseases when administered with other anti-ischemic/anti-inflammatory compositions. As used herein, the term "treatment" or "treatment agent" includes a meaning of "treatment aid" or "therapeutic adjuvant".

As used herein, the term "ischemic disease" refers to a disease of tissue necrosis through a reduction in the blood flow rate and a blockage of blood supply, caused by blood leakage, embolism, or infarction due to injuries of blood vessels.

According to an embodiment of the present invention, the ischemic disease that can be treated by the composition of the present invention is selected from the group consisting of ischemic heart disease, myocardial infarction, angina pectoris, lower limb artery ischemic disease, distal limb ischemic disease, and ischemic cerebrovascular disease.

As used herein, the term "ischemic heart disease" refers to a disease caused by the reduction in blood flow into heart muscle due to the damage, narrowness, and occlusion of coronary arteries for supplying blood to the heart. More specifically, the ischemic heart disease that can be treated by the composition of the present invention is selected from the group consisting of angina, myocardial infarction, and cardiac failure.

As used herein, the term "ischemic cerebrovascular disease" refers to a disease of the damage of brain tissues caused by the non-supply of blood flow due to the damage, narrowness, or occlusion of the brain blood vessels. More specifically, the ischemic cerebrovascular disease is ischemic stroke, and the ischemic stroke includes cerebral hemorrhage and cerebral infarction.

As used herein, the term "neuroinflammatory disease" refers to a disease caused by the damage of neural tissues due to inflammatory responses, and more specifically, refers to neurological damage disease and degenerative nervous system disease, caused by inflammatory responses.

According to an embodiment of the present invention, the neuroinflammatory disease that can be treated by the composition of the present invention is selected from the group consisting of Alzheimer's disease, Parkinson's disease, Huntington's disease, Lou Gehrig's disease, Creutzfeldt Jakob disease, multiple sclerosis, amyotrophic lateral sclerosis, diffuse Lewy body disease, leukencephalitis, temporal lobe epilepsy, and spinal cord injury. Herein, the spinal cord injury may include both inflammatory spinal cord injury and traumatic spinal cord injury.

According to an embodiment of the present invention, in cases where the secretome of human ESC-derived and iPSC-derived neural precursor cells (NPCs) was administered to an experimental ischemic stroke model (permanent Middle cerebral artery occlusion (pMCAO) model), both of the single administration and the multiple administration significantly induced the reduction in ED-1 positive cells and GFAP positive cells compared with the PBS group (FIGS. 8a-8b and 9a-9b). In other words, the secretome reduced the inflammatory response, reduced the number of activated microglial cells (FIGS. 8a-8b), and reduced the number of activated astrocytes (FIGS. 9a-9b).

In addition, the secretome of the present invention increases the number of doublecortin (DCX) expressing neural precursor cells (see FIG. 10). The doublecortin is a marker of migrating neural precursor cells. These results show that endogenous neural stem cells were mobilized in brain tissues due to the administration of the secretome.

The secretome of the present invention increased the number of α-SMA positive vessels, which means an increase in angiogenesis (see FIG. 11).

These anti-inflammatory, endogenous stem cell mobilizing, and angiogenic effects suggest that the neural precursor cell (NPC)-derived secretome has a neuroprotective effect. That is, the neural precursor cell-derived secretome exhibits the above effects, thereby allowing the treatment of neuroinflammatory diseases.

Meanwhile, the secretome of pluripotent stem cell-derived neural precursor cells of the present invention has a treatment effect on spinal cord injury. According to one embodiment of the present invention, the BBB test using a spinal cord injury model showed excellent behavioral recovery in the group injected with pluripotent stem cell (e.g., ESC)-derived neural precursor cells (see FIG. 12). The induced pluripotent stem cells (iPSCs) are considered to be the same as pluripotent stem cells (e.g., embryonic stem cells) since the iPSCs have stem cell gene and protein expression, chromosomal methylation, doubling time, embryoid body formation, teratoma formation, viable chimera formation, hybrid formation, and differentiability, and therefore, the induced pluripotent stem cells also have a treatment effect on such spinal cord injury.

As used herein, the term "administration" or "administer" refers to a method wherein a therapeutically effective amount of the composition of the present invention is directly administered to a subject to form the same amount thereof in the body of the subject. Therefore, the term "administer" includes the injection of an active ingredient (a secretome of PSA-NCAM-positive neural precursor cell, NPC) around a site of lesion, and thus the term "administer" is used in the same meaning as the term "inject".

The term "therapeutically effective amount" of the composition refers to the content, which is sufficient to provide a therapeutic or prophylactic effect to a subject to be administered, and thus the term has a meaning including "prophylactically effective amount". As used herein, the term "subject" includes, but is not limited to, human, mouse, rat, guinea pig, dog, cat, horse, cow, pig, monkey, chimpanzee, beaver, or rhesus monkey. Specifically, the subject of the present invention is human.

In cases where the composition of the present invention is prepared as a pharmaceutical composition, the pharmaceutical composition of the present invention comprises a pharmaceutically acceptable carrier. The pharmaceutically acceptable carrier contained in the pharmaceutical composition of the present invention is one that is conventionally used in the formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, saline, phosphate buffered saline (PBS), and media.

The pharmaceutical composition of the present invention may further comprise, in addition to the above ingredients, a lubricant, a wetting agent, a sweetening agent, a flavoring agent, an emulsifier, a suspending agent, a preservative, and the like. Suitable pharmaceutically acceptable carriers and preparations are described in detail in *Remington's Pharmaceutical Sciences* (19th ed., 1995).

The pharmaceutical composition of the present invention may be administered orally or parenterally. Specifically, the pharmaceutical composition may be injected through parenteral administration, and more specifically, intramuscular administration, intracerebroventricular administration, wound (injured) site administration, spinal cord or intrathecal administration, or intravascular administration. The intravascular administration may include intraarterial or intravenous administration.

A suitable dose of the pharmaceutical composition of the present invention may vary depending on various factors, such as the method for formulation, the manner of administration, the age, body weight, gender, morbidity, and diet of the patient, time of administration, route of administration, excretion rate, and response sensitivity.

The pharmaceutical composition of the present invention may be administered in a single dose or multiple doses. For example, the pharmaceutical composition of the present invention may be administered to human or other animals in a single dose or multiple divided doses. The single-dose composition may fill a daily dose by containing a certain range of amount or a content corresponding to a portion thereof. That is, the composition for treatment according to the present invention may be administered to a patient in need of a treatment in a single daily dose or multiple daily doses, or may be administered in a single dose or multiple doses at intervals of a predetermined time (hour, day, week, etc.).

As used herein, the term "single-dose administration" means a use of a composition comprising a single dose of secretome or a composition administered in a single-dose form, and "multiple-dose administration" means a use of a composition comprising a multiple dose of secretome or a composition administered in a multiple-dose form.

According to an embodiment of the present invention, in cases where the neural precursor cell (NPC)-derived secretome was administered to an ischemic stroke animal model in a single dose, the area of ischemic lesion was decreased, and the behavior improvement effect was observed (see FIGS. 1 to 4).

Meanwhile, even in cases where the neural precursor cell (NPC)-derived secretome was administered to an ischemic stroke animal model in multiple doses, the area of ischemic lesion was decreased, and the behavior improvement effect was observed (see FIGS. 6a to 6i and 7). Especially, a multiple-dose group, compared with a single-dose group, showed a higher treatment effect on the behavioral improvement (FIGS. 6a-6i) and a higher anti-inflammatory effect (FIGS. 8a-8b and 9a-9b), and it was confirmed that the repeated administration of secretome significantly increased endogenous neural stem cells and the number of new vessels.

The pharmaceutical composition of the present invention may be formulated into a unit dosage form or may be prepared in a multi-dose container by using a pharmaceutically acceptable carrier and/or excipient according to the method easily conducted by a person having an ordinary skill in the art to which the present invention pertains. Here, the dosage form may be a solution in an oily or aqueous medium, a suspension, a syrup, or an emulsion; an extract, a pulvis, a powder, a granule, a tablet, or a capsule; and may further include a dispersant or a stabilizer.

In accordance with another aspect of the present invention, there is provided a method for preventing or treating ischemic disease or neuroinflammatory disease, the method comprising administering, to a subject, a composition comprising: (a) a therapeutically effective amount of the secretome derived from neural precursor cells (NPCs); and (b) a pharmaceutically acceptable carrier.

Since the method of the present invention uses the above-described composition of the present invention, descriptions of overlapping contents therebetween are omitted to avoid excessive complication of the specification due to repeated descriptions thereof.

Advantageous Effects

The features and advantages of the present invention are summarized as follows:

(i) The present invention provides a composition comprising the secretome of neural precursor cells (NPCs) as an active ingredient for treating ischemic diseases or neuroinflammatory diseases.

(ii) The secretome of the neural precursor cells of the present invention reduces the area of ischemic injury and restores nerve functions through roles thereof, such as anti-inflammation, angiogenesis, and mobilization and proliferation of endogenous stem cells, and thus the secretome can be used as a therapeutic agent for cerebral ischemic diseases, neurological damage disease caused by inflammation, and degenerative nervous system diseases.

(iii) Furthermore, the secretome of the neural precursor cells of the present invention showed a very excellent behavioral improvement effect in a multiple-dose administration compared with a single-dose administration.

BRIEF DESCRIPTION OF THE DRAWINGS

FIG. 3a shows beam balance test result; FIG. 3b shows prehensile traction test results; FIG. 3c shows foot fault test results; FIG. 3d shows line cross results indicating the activeness of behavior per unit time.

In FIGS. 6a to 6i, white: control group, black: medium control group, yellow: secretome single-does treatment group (Secretome-S), red: secretome four-dose treatment group (Secretome-M), *P value<0.05, P value<0.01, *P<0.001.

MODE FOR CARRYING OUT THE INVENTION

Figure 1:
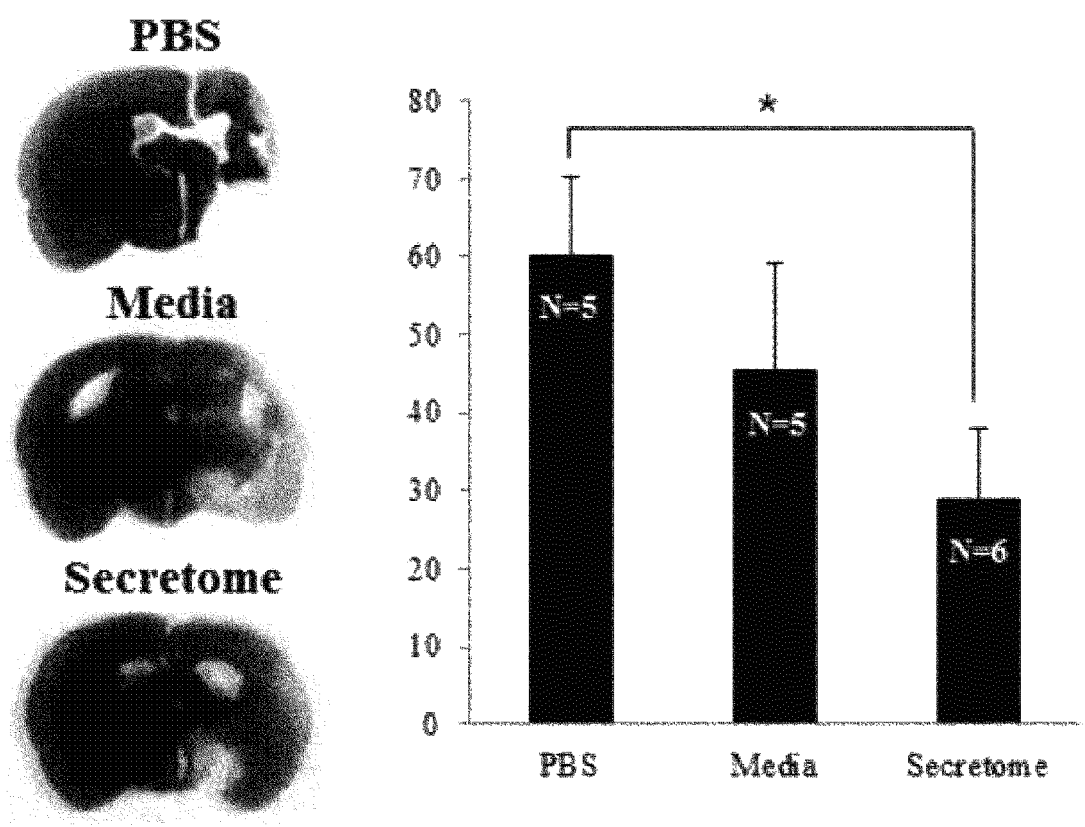
FIG. 1 shows the size of an ischemic lesion site in a PBS control group, a medium control group, and a group treated with the secretome of human embryonic stem cell (ESC)-derived neural precursor cells (NPCs).

Hereinafter, the present invention will be described in detail with reference to examples. These examples are only for illustrating the present invention more specifically, and it will be apparent to those skilled in the art that the scope of the present invention is not limited by these examples.

EXAMPLES

Materials and Methods

Obtaining Human ESC-Derived or Human iPSC-Derived NPC and PSA-NCAM-Positive NPC Cells The use of human cells was approved by the Institutional Review Board (IRB No. 4-2008-0643). For neural induction, embryoid bodies (EBs) derived from hESCs were cultured for 4 days in suspension with 5 μM dorsomorphin (DM) (Sigma, St. Louis, Mo.) and 5-10 μM SB431542 (SB) (Calbiochem, San Diego, Calif.) in hESC medium deprived of bFGF (Invitrogen), and then attached on Matrigel-coated dishes (BD Biosciences, Bedford, Mass.) in 1×N2 (Invitrogen) media supplemented with 20 ng/ml bFGF for the additional 5 days (Kim, D. S., Lee, D. R., Kim, H. S., et al. (2012). *PLoS One*, 7, e39715). Neural rosettes that appeared in the center of attached EB colonies were carefully isolated using pulled glass pipettes from the surrounding flat cells. Small rosette clumps were then seeded on Matrigel-coated dishes after gentle trituration and cultured in DMEM/F12 supplemented with 1×N2, 1×B27 (all from Invitrogen) (referred to as N2B27 medium) plus 20 ng/ml bFGF (Kim, D. S., Lee, J. S., Leem, J. W., et al. (2010). *Stem Cell Reviews and Reports*, 6, 270-281).

Neural precursor cells (NPCs) from neural rosettes expanded upon reaching approximately 80-90% confluence were obtained, and then were exposed to 10 μM Y27632 (Sigma) for 1 hour to prevent apoptosis prior to being subjected to MACS procedure. After dissociation using Accutase (Invitrogen), the cells (~1×10$^8$ cells) were blocked in 1% BSA-containing PBS, and then incubated together with anti-PSA-NCAM antibody conjugated with microbeads (Miltenyi Biotec) at 4° C. for 15 minutes. After extensive washing, the cell suspension was loaded in magnetic activated cell sorting (MASC), and positively-labeled cells that remained on the column were eluted to the MACS exclusive tube. The isolated PSA-NCAM positive neural precursor cells (NPCs) were plated at a concentration of 4-5×10$^5$ cells/cm$^2$ in N2B27 media or NBG media supplemented with 20 ng/mL bFGF (1×N2, 0.5×B27, and 0.5×G21 supplement) (GeminiBio-Products, West Sacramento, Calif.). The culture media were changed every day and cells were passaged every 2-3 days.

Separation of Secretome from Human Pluripotent Embryonic Stem Cell (ESC)-Derived Neural Precursor Cells (NPCs)

The obtained human pluripotent embryonic stem cell (ESC)-neural precursor cells (PSA-NCAM-positive neural precursor cells) were repeatedly cultured and amplified for 4 passages or more in a Matrigel-coated 60-mm dish with N2 serum-free supplement (100×-final concentration 1×), B-27 (50×-final concentration 0.5×) and Gem21 (50×-final concentration 0.5×) and bFGF (20 ng/mL) in a base culture liquid (DMEM/F-12), and then grown in 8-10 dishes until the cells reached 90% confluency. Following removal of the culture liquid, the cells were washed three times with phosphate buffered saline, and cultured for 24 h in a serum-free base culture liquid (DMEM/F12) supplemented with only ITS (100×-final concentration 1×) and bFGF (20 ng/mL). For a control, the same amount of base culture liquid with the same composition (base culture liquid supplemented with the same amount of ITS and bFGF) was put in a dish without cells, and incubated in an incubator for 24 h, and then collected. The culture liquid was all collected and centrifuged (800 g at 30 min) to remove cell debris and dead cells, and then directly frozen in a freezer at −70° C., and, when necessary, was thawed before use.

Separation of Secretome from Human Induced Pluripotent Stem Cell (iPSC)-Derived Neural Precursor Cells (NPCs)

Human pluripotent induced pluripotent stem cell (iPSC)-derived neural precursor cells (NPCs) at P$_0$ were subcultured up to P$_4$ in a Matrigel-coated 100-mm dish with a base culture (DMEM/F-12) in which N2 serum-free supplement, B-27, and Gem21 were put and bFGF was added, until the cells reached at least about 90% confluence. Thereafter, the culture liquid was removed, and then the cells were washed once with a phosphate buffer solution, separated from the dish using Accutase enzyme, and then washed two or three times with PBS. In addition, only ITS was added to the DMEM base culture liquid not containing phenol red, and then the cells were cultured in a floating state for 24 hours. As a control group of the culture liquid, a culture liquid obtained by adding an equal amount of ITS to an equal amount of a base culture liquid and then incubating cells in an incubator for 24 hours was used. The culture liquid with floating cells was all collected, and centrifuged (1,000 g for 20 min) to remove cell debris and dead cells, and then directly frozen in a freezer at −70° C., and, when necessary, was thawed before use.

Cell culture conditions are follows:

(1) basic cell culture conditions—DMEM/F-12, bFGF 20 ng/ml, N2 100×-final concentration 1×, B-27 50×-final concentration 0.5×, Gem21 50×-final concentration 0.5×

(2) culture conditions for obtaining secretome—DMEM/phenol red free, ITS 100×-final concentration 1×

Establishment of Stroke Model

In order to measure the neural protective effects against neural damage due to local ischemic stroke, an intraluminal suture method was used. This method is a local ischemic stroke model developed by Zea Longa (Zea Longa, et al, Stroke., 1989, 20, 84-91), and has an advantage of clinical similarity, unlike other models. For this reason, this model is suitable to research ischemia-reperfusion mechanism or to screen effects of several drugs. The local ischemic model has, in addition to the foregoing advantages, an advantage in that both the reperfusion injury due to transient middle cerebral artery occlusion and the continuous cell injury due to permanent middle cerebral artery occlusion can be observed using a probe. The difference between an ischemic core and an ischemic penumbra is made by the cerebral blood flow. The cerebral blood flow is less than 15% in the former and less than 40% in the latter. The nerve cells in the center die sporadically for occlusion for 10-20 minutes; a core is formed and the brain tissue injury is enlarged for occlusion for 1 hour; and an injury similar to permanent occlusion occurs after occlusion for 2-3 hours.

After acclimatization for one week, animals (male Sprague-Dawley rat, body weight 250-300 g) were anesthetized using a respiration anesthetic machine, and isoflurane was used for an anesthetic drug. White rats were first subjected to general anesthesia using a mixture gas of 80% N$_2$O and 20% O$_2$, and 5% isoflurane, which was then maintained at 2-2.5% for anesthesia. For the establishment of stroke model, the left neck skin of the white rats was incised, and then the common carotid artery, external carotid artery, and internal carotid artery were isolated, and the respective arteries were slightly tied with a black silk thread to block the blood flow. A small hole is cut in the common carotid artery, and the 25-mm 4-0 nylon probe with an end of 0.40 mm, obtained by rounding the end of the nylon suture using cautery, was inserted through the cut section. The nylon probe inserted into the external carotid artery was inserted and fixed into the middle cerebral artery via the internal carotid artery. After the probe is inserted at about 18-20 mm from the branch site of the common carotid artery, the origin of the middle cerebral artery was blocked, and then fixed by a thread to permanently occlude the middle cerebral artery. Thereafter, the skin incision site was again sutured, and then the rats were naturally recovered from the anesthesia.

Injection of Secretome into Stroke Model through Cerebral Artery and Behavioral Test:

a. Injection of Secretome of Human ESC-Derived Neural Precursor Cells (NPCs)

After the baseline for the behavioral test was established one day after stroke induction, an insulin syringe needle was inserted into the internal carotid artery via the right external carotid artery in the same manner as stroke model establishment, and through the needle, 0.2 mg/kg (injection volume 50 μl) of the secretome was intraarterially injected, and the same volume of the culture liquid or phosphate buffered saline (PBS) was administered as a control. After the injection of the secretome liquid, the conditions of the animals were observed for 14 days. The weight measurement was conducted once before injection and four times after injection, and behavioral analysis was conducted.

b. Injection of Secretome of Human iPSC-Derived Neural Precursor Cells (NPCs)—Multiple-Dose Administration After the baseline for the behavioral test was established one day after stroke induction, an insulin syringe needle was inserted into the internal carotid artery via the right external carotid artery in the same manner as in the stroke model establishment, and through the needle, 0.2 mg/kg (60 μg for 300 g of rat, injection volume 200 μl) of the secretome was intravenously injected (administered through penile vein). The same volume of a culture liquid was administered to a control group. A culture liquid obtained by adding an equal amount of ITS to an equal amount of a base culture liquid and then incubating cells in an incubator for 24 hours was used as a control group of the secretome, like in the isolation of the proteome. After the injection of the secretome liquid, the conditions of the animals were observed for 14 days. The weight measurement was conducted once before injection (day 0) and four times after injection (day 3, day 7, day 10, and day 14), and behavioral analysis was conducted.

c. Behavioral Analysis

1) Torso twisting test: In order to test the upper body posture considered as the sense of the cerebral cortex and striatum of animals, asymmetric behavior was measured.

2) Beam balance test: The gross vestibulomotor function was evaluated through steady posture of the animals on the narrow beam.

3) Foot-fault test: This test is used when the adjustment (cooperation) and unification (integration) of the motor movement are tested. The foot fault is defined that the paw falls between the grid bars or the rat misplaces a forelimb or hind-limb. The foot fault is symmetric in normal animals.

4) Prehensile Traction test: The prehensile portion of the test involves the rat's ability to hang onto the horizontal rope by its forepaws. The prehensile traction test was used to measure the rat's muscle strength. This test was adapted from similar tests described previously. The steel bar (2-cm diameter, 100-cm length) was placed horizontally 70 cm above the sponge rubber pad (7.5 cm thickness). The rat's forepaws were placed on the steel bar and the animal was released. The animals were allowed to hang onto the steel bar for up to 5 s. Time of falling was noted as well as whether or not the animals brought the rear limb up to the bar with the following scores; score 0—the rat hangs on for 5 s and brings rear limb up, score 1—rat hangs on for 5 s and no rear limb is brought up, score 2—rat hangs on for 3-4 s, score 3—the rat hangs on for 0-2 s.

5) Open-field test: This test is used to find out general walking activity levels. The activity, emotion, and behavioral patterns of the animals were measured by directly measuring the behavioral aspects and characteristics.

6) Modified Neural Severity Score (mNSS): The score is a total score of motor, sensory, balance, reaction, and emotion test values obtained through the above various tests, and the score is calculated by the following criteria (mNSS is measured by adding up scores for each subject).

Open Field Test (Measuring Emotion, Activity, and Behavioral Patterns of Animals).
No movement: 3
1-20: 2
21-30: 1
30 or more: 0
Prehensile Traction Test (Muscular Measurement)
0-5 s: 3
6-10 s: 2
11-20 s: 1
21 s or over: 0
Beam Balance Test (Measurement of Sense of Balance)
Score 0: 1=Stable posture
2=grasps side of beam and has shaky movement
Score 1: 3=one or more paws slip off beam.
4=attempts to balance on the beam but falls off
Score 2: 5=drapes over the beam but falls off.
6=falls off the beam with no attempt to balance Foot Fault Test (Motor Cooperation Ability)
0-5 s: 0
6-10 s: 1
11-20 s: 2
21 s or above: 3
Upper Body Posture Test (Asymmetric Behavior Test)
0: 2
1-4: 1
5 or more: 0

The rats were anesthetized with zoletil 14 days after ischemic induction, and subjected to lung open and right auricle incision. A needle was injected into the left ventricle, and then, the heart was perfused with PBS using a pump to remove blood flow, and then the brain tissue was extracted. The tissue sections for sample construction were embedded in paraffin on the basis of bregma. For verification of damaged brain tissue, the brain tissue sections were stained with haematoxylin and dehydrated, and the slide was photographed using a digital camera, and then transferred to a computer. The percentage of infarction area was calculated by formula 1 using an image analysis program (image J).

Percentage of infarct (%)=(the area of the contralateral hemisphere−the intact area of the ipsilateral hemisphere)/the area of the contralateral hemisphere×100    Formula 1

Immunohistochemical Analysis and Quantification

The brain tissues were fixed with 4% formaldehyde for 24 hours, and washed with PBS. For paraffin section preparation, the tissues were dehydrated in cumulative ethanol, and paraffin-embedded. The paraffin-embedded brain tissues were cut into 4 μm-thick layers on a microtome, deparaffinized in xylene for 10 minutes, and then rehydrated in cumulative alcohol. The slices were treated with 10 mM citric acid for 1 hour, and then 5% BSA solution containing PBS and 0.5% Triton X-100 was added. Thereafter, the brain tissue slices were cultured at 4° C. for 15-17 hours together with primary antibodies against ED-1 (Abcam) (1:100), doublecortin (DCX; Abcam, 1:100), glial fibrous acidic protein (GFAP; Millipore, 1:100), and α-smooth muscle actin (aSMA; Abcam, 1:100) for 15-17 hours. The slices were cultured together with the primary antibody overnight, and then washed with PBS, and then the slices were cultured together with fluorescence-labeled secondary antibodies (Alexa-Fluor®488 or 594, 1500, Molecular Probes, Eugene, Oreg., USA) for 1 hour. Fluorescence images of the slices were obtained using a fluorescence microscope (Olympus IX71).

Secretomics

The secretome of neural precursor cells derived from hESC and the secretome of neural precursor cells derived from human iPSC were separated on SDS-PAGE using 4-12% gradient Novex Bis-Tris gel (Invitrogen), and then gels were stained with Gel Code Blue staining reagent (Piece) to show protein bands. The stained gels were cut into 10 bands with the same size, which were then subjected to In-Gel Tryptic Digestion by a known method.

The peptides prepared by the In-gel tryptic digestion were analyzed by the LinearTrap Quadrupole (LTQ) mass spectrometer (Thermo Finnigan) coupled with Nano Ultra Performance liquid chromatography (Eksigent Technologies). Specifically, trypsinized peptides were applied to an analytical column (75 μm×11 cm) packed with C18 regular 5 μm-sized resin. A linear 45 min gradient was achieved from 97% solvent A (0.1% formic acid in distilled water) to 60% solvent B (0.1% formic acid in acetonitrile) at a flow rate of 0.3 μl/min. The separated peptide ions were electrosprayed into the nano-electrospray ionisation (ESI) source. All MS/MS spectra were acquired by data-dependent scans in which the five most abundant spectra from the full MS scan were selected for fragmentation. The repeat count for dynamic exclusion was set to 1, the repeat duration was 30 s, the dynamic exclusion duration was set to 180 s, the exclusion mass width was 1.5 Da, and the list of dynamic exclusion was 50.

The identification of peptides and proteins was researched from ipi.HUMAN v3.76 database (89 378 entries) using Turbo-SEQUEST algorithm (Thermo Finnigan). Following database research, the identified peptides and proteins were confirmed using scaffold 2 (Proteome Software). Among the peptides obtained from the SEQUEST search, a set of peptides with a PeptideProphet probability greater than 0.95 was selected. Furthermore, a list of proteins that had a ProteinProphet probability greater than 0.99 and also had more than two unique peptides obtained.

Establishment of Spinal Cord Injury (SCI) Model, Injection of Secretome, and Behavioral Recovery Test (BBB Score Test)

After experimental animals (male Sprague-Dawley rats, body weight: 250-300 g) were anesthetized, spinal bone removal was carried out (laminectomy). A 10-g rod was dropped onto the exposed spinal cord using an NYU impactor, causing spinal cord injury (SCI modeling). After the wound was well disinfected, the skin was sutured. After the injury of the spinal cord, the secretome of pluripotent embryonic stem cells (i.e., ESC)-derived neural precursor cells (NPCs) of the present invention was injected into a site of the wound. Thereafter, the secretome was intravenously administered two more at an interval of about 3 days. After the injection of the secretome, the BBB test was carried out every week. After the BBB test for 8 weeks or longer, comparison with the control group was carried out.

Statistical Analysis

The statistical significance among groups was obtained using one-way analysis of variance (ANOVA) with Tukey's correction, and a p value <0.05 was determined to be statistically significant.

Result 1: Secretome of Human Embryonic Stem Cells (ESC)-Derived Neural Precursor Cells In order to investigate the alleviation of a disease through the secretome of human ESC-derived neural precursor cells (NPCs) in the stroke model, the following three groups were tested for 2 weeks. At 24 h after stroke induction, white rats with the induced disease confirmed by the behavior test were arbitrarily allocated into three groups, and an equal volume (50 μl) of secretome (0.2 mg/kg, volume 50 μl), medium, or PBS was injected into the right external carotid artery. The conditions and weights of animals were monitored at 3, 7, 10, and 14 days after the injection of each material, and behavior analysis was performed.

TABLE 1

| Group | Description |
| --- | --- |
| PBS control | PBS-treated group after stroke induction |
| Medium control | Stroke animal treated with basal Medium |
| Secretome-treated group | Stroke animal treated with cultured medium (secretome) derived from neural precursor cell culture |

Ischemic Lesion Analysis Results

The induction of stroke through permanent MCAO in rats induced extensive brain lesion. The brain was extracted 14 days after the stroke induction, and then the damage and the damaged sites of the brain were confirmed by TTC (2,3,5-triphenyltetrazolium chloride) staining. TTC staining occurs by a reaction with normal mitochondrial oxidative enzyme system in cells, and the damaged mitochondria by ischemic damage are not stained due to the disturbance of the oxidative system, showing white, which can differentiate the damaged sites of the brain.

As shown in FIG. 1, the damage induced by middle cerebral artery occlusion mainly appeared on the cortex and striatum (FIG. 1). The injection of the secretome of neural precursor cells reduced the ischemic lesion area (infarct size). The PBS control showed approximately the damage of 60% of the right brain and the medium control showed about 46%, but the secretome-treated group showed a damaged site of about 29%, which was significantly reduced compared with the controls.

Body Weight Analysis Results

Figure 2:
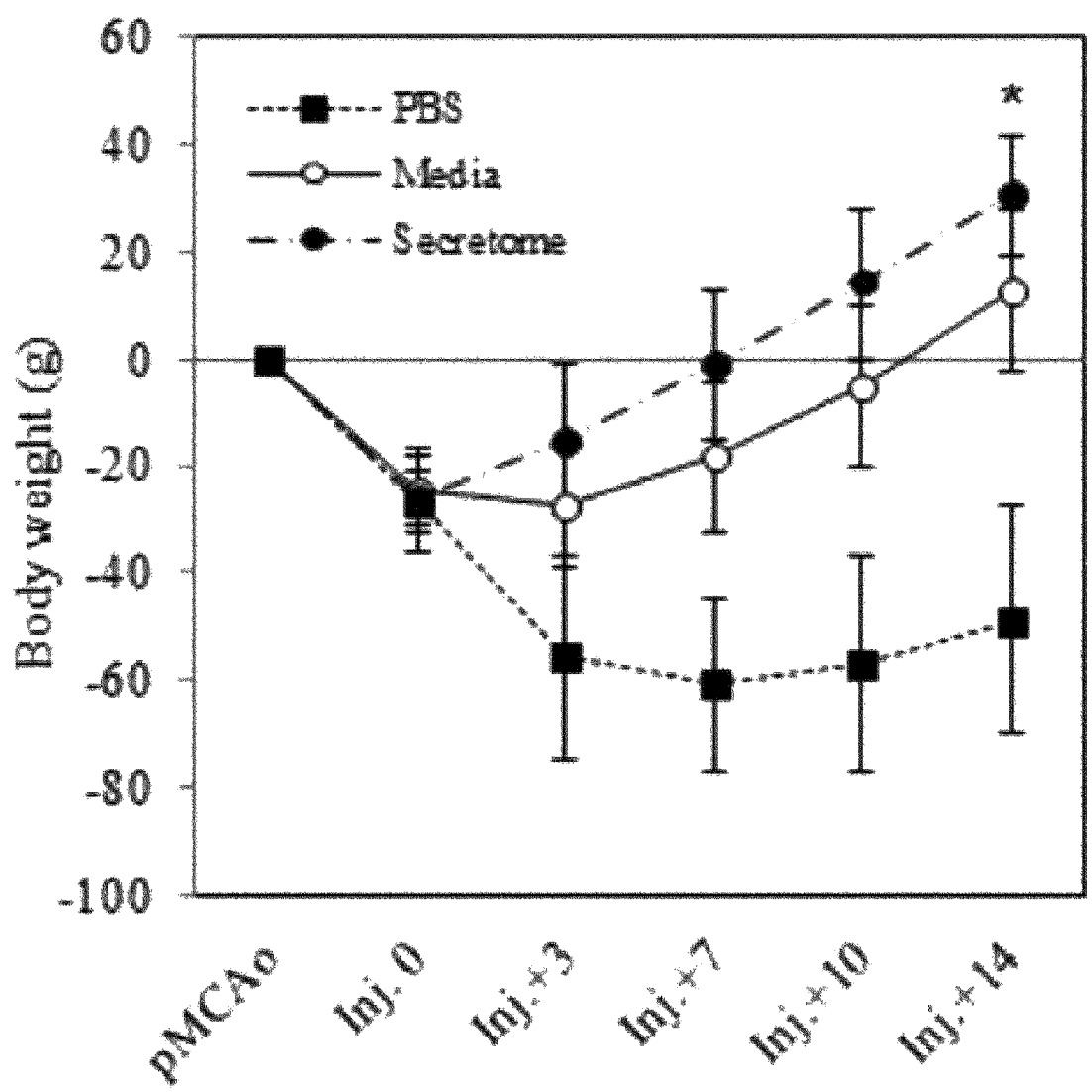
FIG. 2 illustrates the change in body weight in the PBS control group, medium control group, and secretome-treated group.

The stroke induction reduces the motor performance of rats, the immediate weight loss was advanced by 7 days, and various treatment agents induced the body weight increase through the recovery of motor performance. The injection of the secretome also induced the body weight increase similar to cell transplantation (FIG. 2). The recovery of body weight was notable in recovery of the neural damage. The secretome-treated group showed a significant improvement compared with the PBS control.

Behavior Analysis Results

Figure 3A:
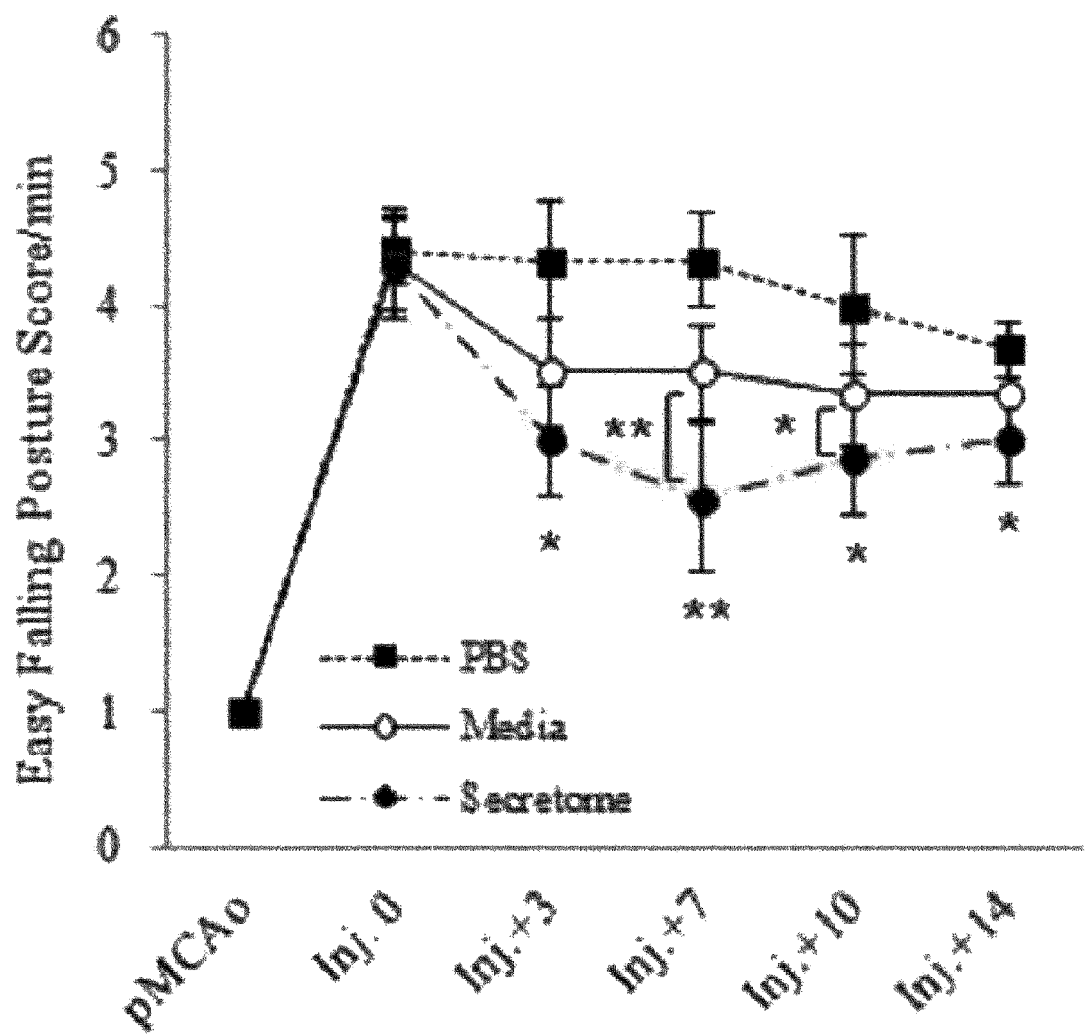
FIGS. 3a to 3d illustrate behavior analysis results in the PBS control group, medium control group, and secretome-treated group.

The secretome-treated group showed a statistically significant behavior improvement effect compared with the two controls in the beam balance test, and there was an immediate effect, for example, the effect was exhibited from day 3 post-treatment (FIG. 3a).

Figure 3B:
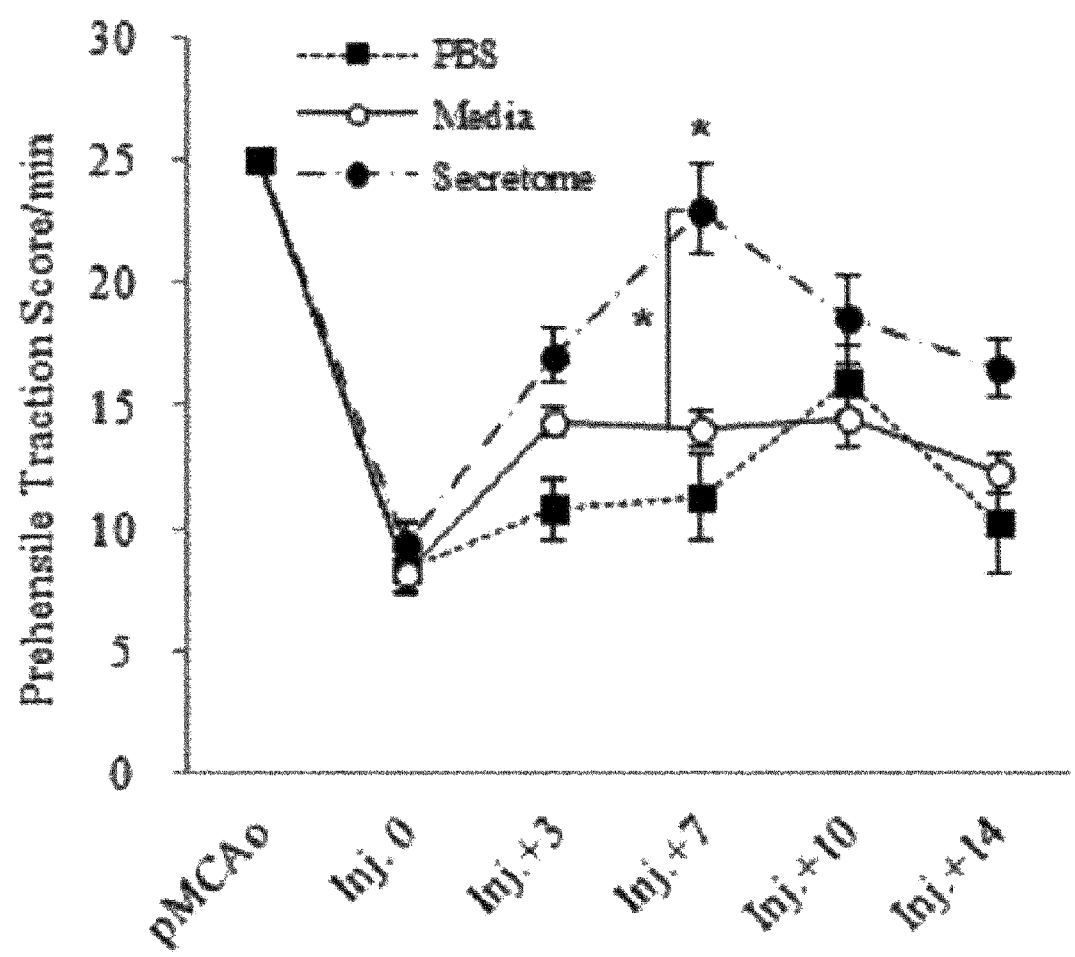

In addition, the secretome-treated group showed a statistically significant effect compared with the two controls on day 7 post-treatment (injection) in the prehensile traction test (FIG. 3b).

Figure 3C:
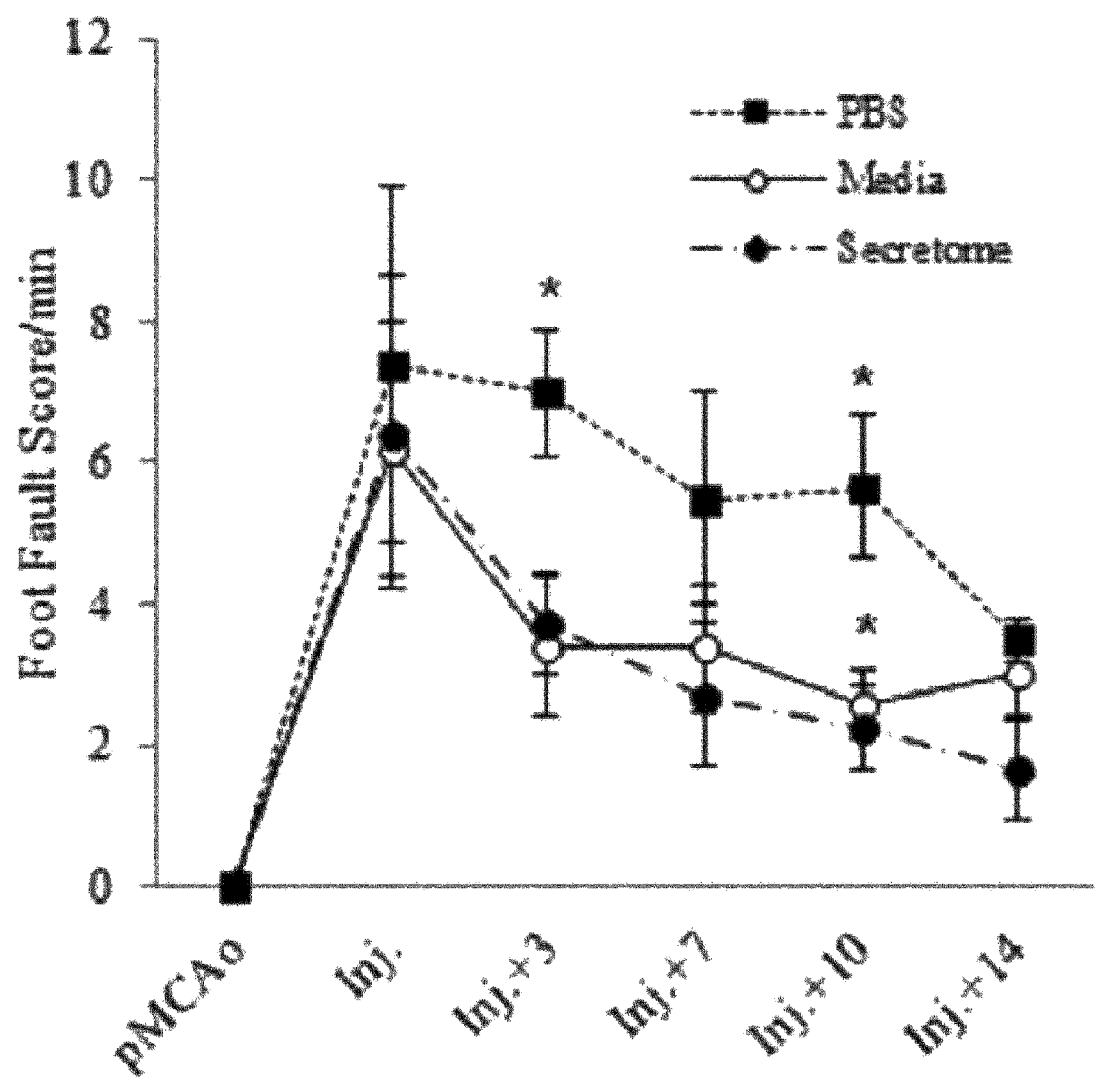
Figure 3D:
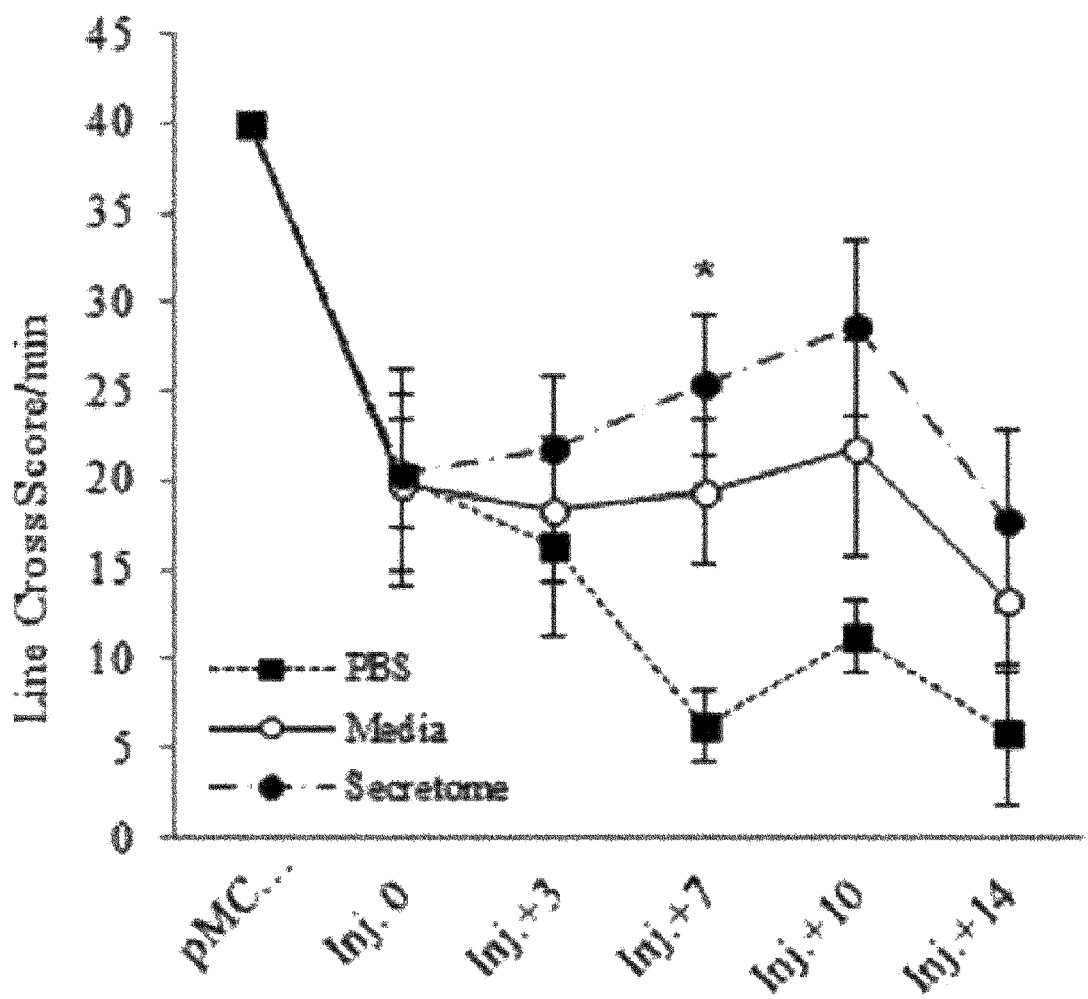

Further, the injection of the secretome showed the reduction effect in the foot fault frequency in a net (FIG. 3c). The injection of the secretome also showed an improvement in the line cross for measuring the activeness of behavior per unit time (FIG. 3d).

Modified Neurological Severity Score (mNSS) Analysis

Figure 4:
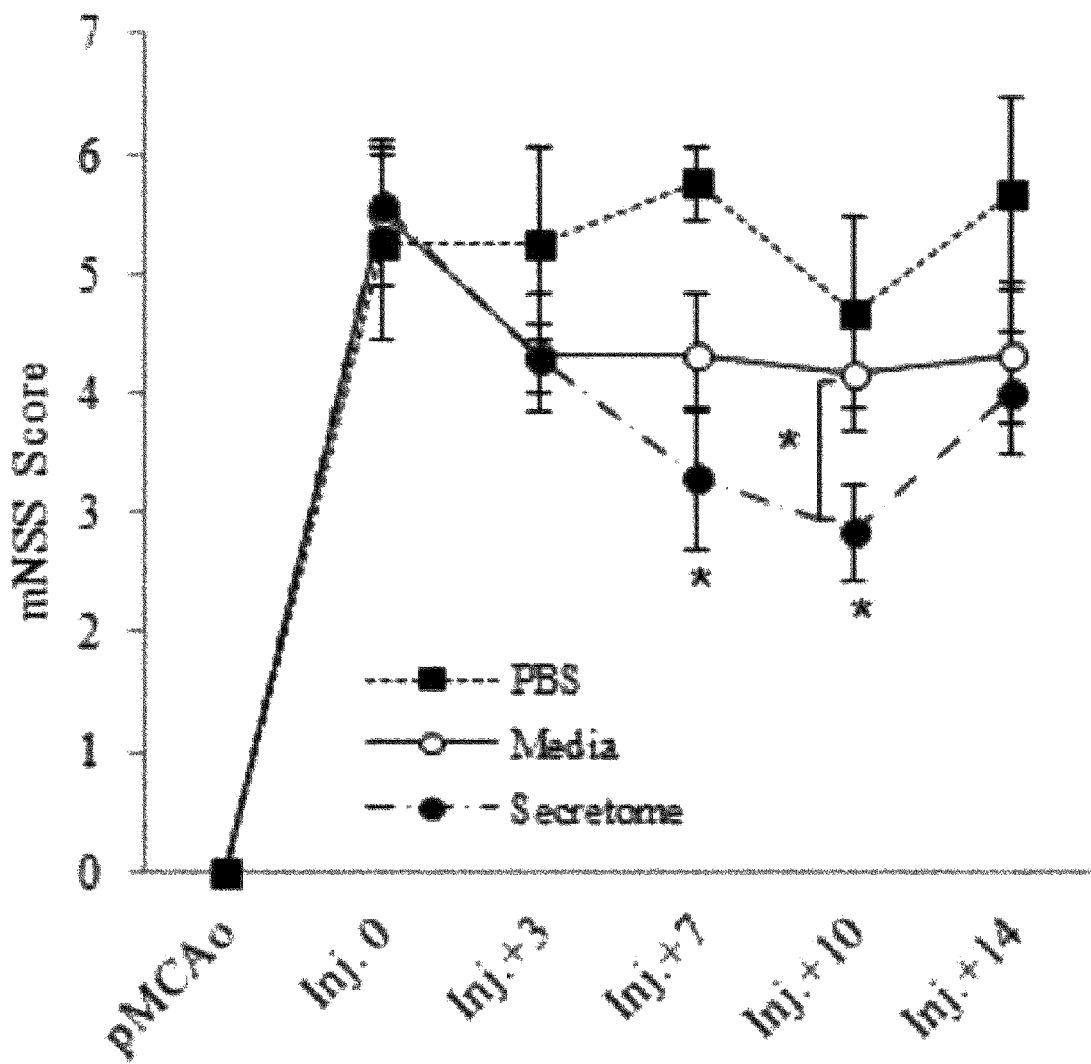
FIG. 4 shows comprehensive behavioral analysis of modified neurological severity scores (mNSS) from FIG. 3 results in PBS control group, medium control group, and secretome-treated group. *P value<0.05, **P value<0.01 in FIGS. 1 to 4.

The modified neurological severity score (mNSS) test is a composite table for measuring neurological functions. Motor (muscle state) and sensory (vision, touch, and proproceptive) items were evaluated. Normal score is 0, and the higher score, the more severe is the dysfunctions. As shown in FIG. 4, the secretome-treated group showed a significantly higher treatment effect (behavior improvement) from the early treatment in the mNSS analysis, compared with the PBS control and the medium control (FIG. 4).

In the mNSS test, the PBS control showed that the average score was 5.4 n day 1 and 5.5 on day 14 after the ischemic induction, indicating that the neurobehavioral disorders caused by stroke was maintained. The medium control showed a temporary behavior improvement effect on day 3 of treatment, but did not exert an additional improvement effect. Whereas, the secretome-treated group showed a continuous behavior improvement effect from day 3 of treatment (mNSS score: 4.5) to day 10 of treatment (mNSS score: 3).

Secretome Analysis

The secretome obtained from neural precursor cells derived from iPSCs includes the following proteins: Agrin, annexin A5, BSG (Basigin), biglycan, calponin-3, coactosin-like protein, cofilin-1, collagen alpha-2, cullin-3, destrin, dystroglycan, ephrin-B2, exportin-2, ezrin, fibronectin, fibulin-1, frizzled-related protein, gelatin-3 binding protein, granulins, growth/differentiation factor 11, haptoglobin, hemopexin, high mobility group protein B2, hornerin, importin-9, insulin-like growth factor-binding protein 2, Lupus La protein, macrophage migration inhibitory factor, midkine, moesin, neuropilin 2, pleiotrophin, profilin-1, protein DJ-1, radixin, secreted frizzled-related protein-2, septin-11, talin-1, testican, thymopoietin, transgelin-3 and vimentin.

The secretome obtained from neural precursor cells derived from human embryonic stem cells includes the following proteins: Agrin, annexin A2, attractin, biglycan, ceruloplasmin, cofilin-1, collagen alpha-1, coronin-1x, dermicidin, DERP12, eprin-B3, exostosin-2, ezrin, gelatin-3 binding protein, granulins, growth/differentiation factor 11, haptoglobin, hemopexin, high mobility group protein B2, hornerin, insulin-like growth factor-binding protein 2, Lupus La protein, midkine, moesin, multiple epidermal growth factor-like domains protein 8, nidogen-1, parathymosin, profilin-2, protein DJ-1, secreted frizzled-related protein-2, secretogranin, talin-1, thymosin beta-4, TGFBI (Transforming growth factor-beta-induced protein ig-h3), transgelin and vimentin.

Spinal Cord Injury Treatment Effect

Figure 12:
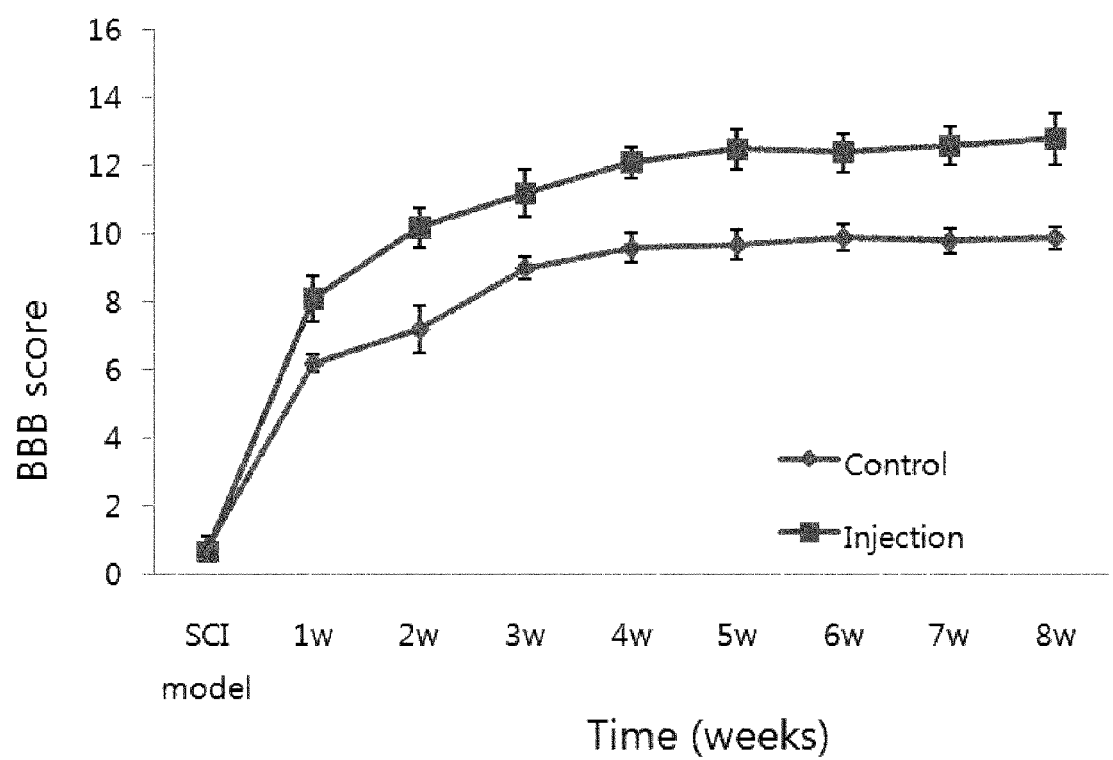
FIG. 12 shows that, when BBB testing was conducted on a spinal cord injury model for 8 weeks or more, the secretome injection group showed excellent behavioral recovery when compared with a non-treatment control group.

Spinal cord injury (SCI) model was established and approximately 30 μl of the secretome of pluripotent stem cells (ESC)-derived neural precursor cells (NPCs) was directly injected into five injury sites. Thereafter, approximately 200 μg (200 μl) of the secretome was injected intravenously twice at approximately 3-day intervals. Weekly behavioral recovery was assessed according to the spinal cord injury recovery test (BBB test). The BBB test is a test method that is commonly well known to spinal cord injury researchers. The BBB test was performed for 8 weeks or more, and showed excellent behavioral recovery in the secretome injection group when compared with the untreated control (FIG. 12).

Figure 5:
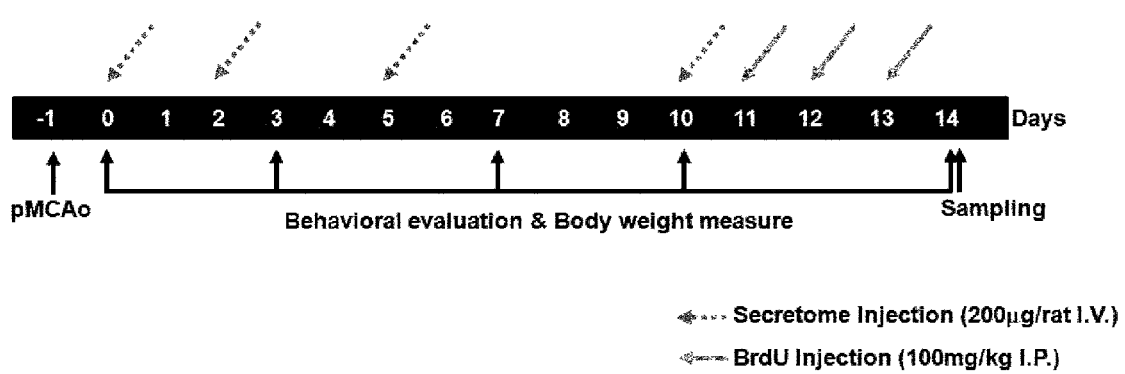
FIG. 5 shows an experimental schedule for investigating the effects of multi-dose administration of the human induced pluripotent stem cell (iPSC)-derived neural precursor cell (NPC)-derived secretome. BrdU was injected to investigate the mobilization of endogenous neural stem cells, which exist in the brain tissue, by the neural stem cell-derived secretome.

Result 2: Secretome of Human Induced Pluripotent Stem Cells (iPSC)-Derived Neural Precursor Cells+Multiple-Dose Administration In order to investigate the alleviation of a disease through single-dose administration and multiple-dose administration of the neural precursor cell (NPC) secretome in the stroke model, the following four groups were tested for 2 weeks. The experimental schedule is shown in FIG. 5.

TABLE 2

| Group | Description |
| --- | --- |
| Control group | No treatment after stroke induction |
| Medium control group | Treatment with medium utilized for the culture of neural precursor cells after stroke induction |
| Secretome single-dose treatment group | Treatment with a single dose of a neural precursor cell conditioned medium after stroke induction |
| Secretome four-dose treatment group | Treatment with four doses of a neural precursor cell conditioned medium after stroke induction |

FIGS. 6a to 6i show the experimental results of single-dose administration vs. four-dose administration of the induced pluripotent stem cell-derived neural precursor cell secretome. It can be seen that excellent behavioral improvement effects were observed in the secretome four-dose treatment group (Secretome-M) compared with the other groups in almost all conditions. That is, it was confirmed that, with respect to behavioral improvement, the multiple-dose administration group showed very significant treatment effects compared with the single-dose administration group.

Body Weight Analysis

Figure 6A:
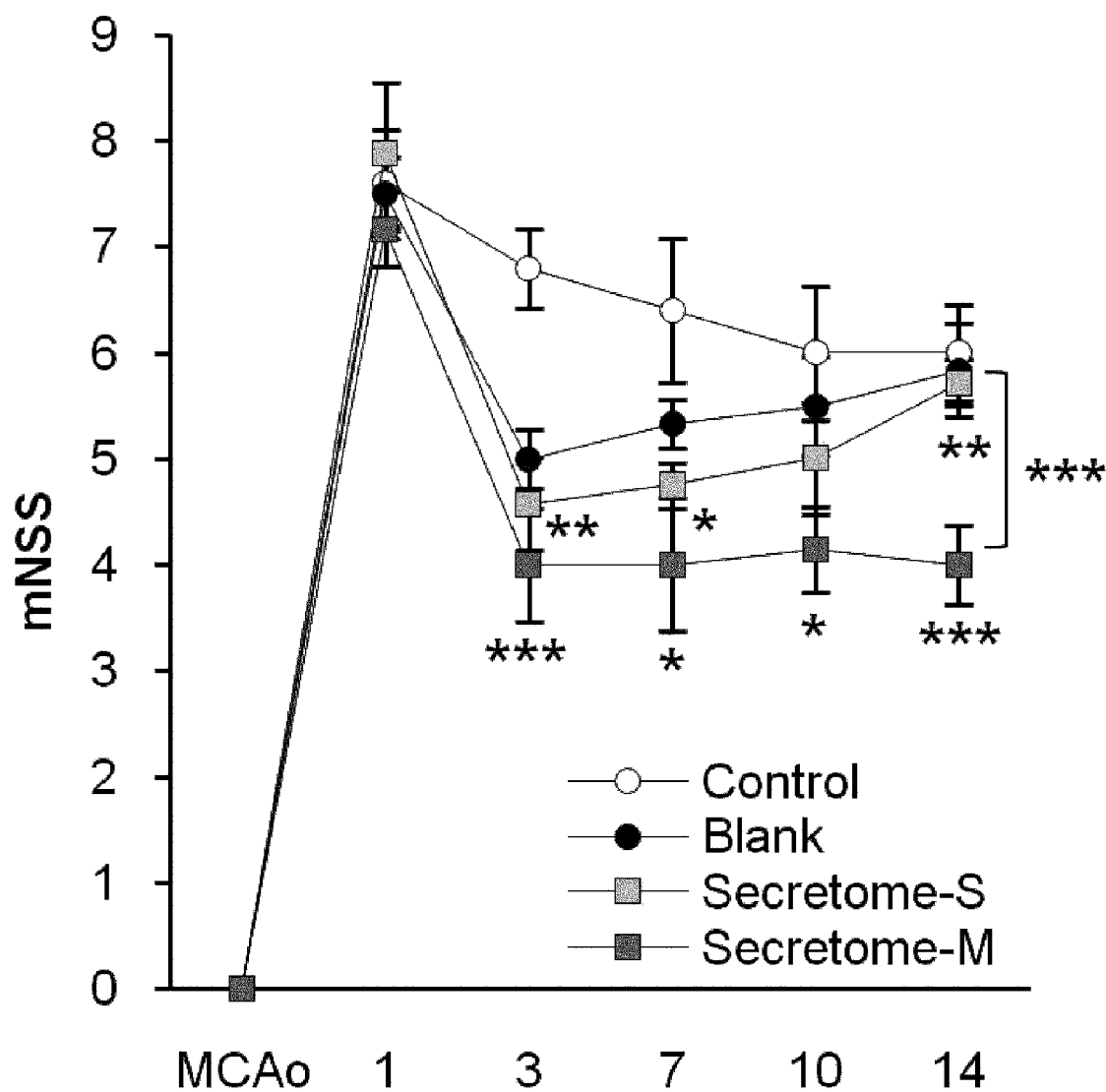
FIGS. 6a to 6i show experimental results of single-dose administration vs. four-dose administration of the pluripotent stem cell-derived neural precursor cell (NPC)-derived secretome. 6a, modified neurological severity score (mNSS); 6b, torso twisting test (left); 6c, torso twisting test (ring); 6d, foot-fault test; 6e, line cross test; 6f, rearing test; 6g, beam balance test; 6h, prehensile traction test; 6i, body weight change in a control group and a secretome treatment group. Rearing refers to the pose of an animal standing upright on its hind legs, and is a general behavior when a normal animal curiously explores. The rearing is represented by the number per unit time.
Figure 6B:
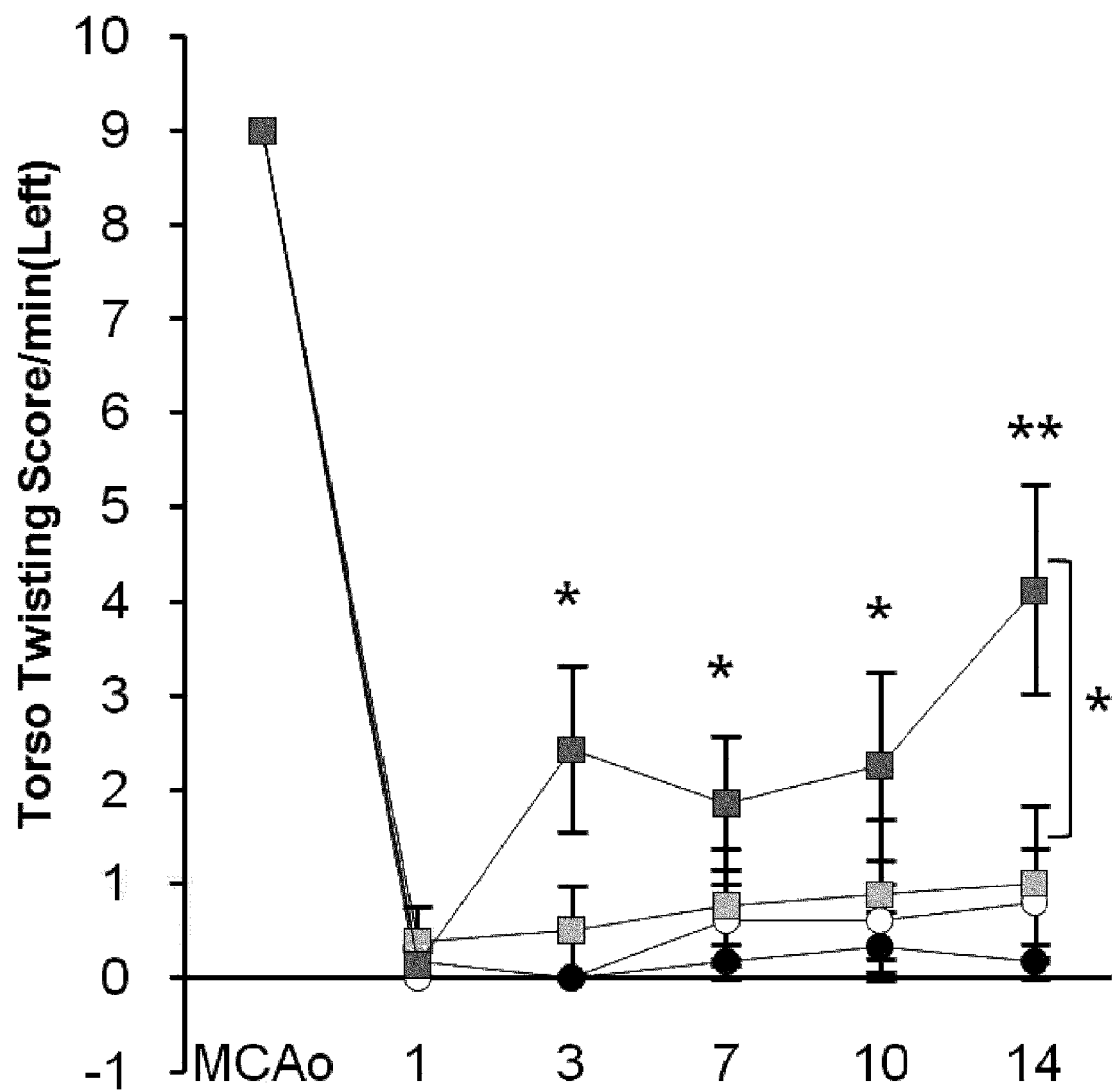
Figure 6C:
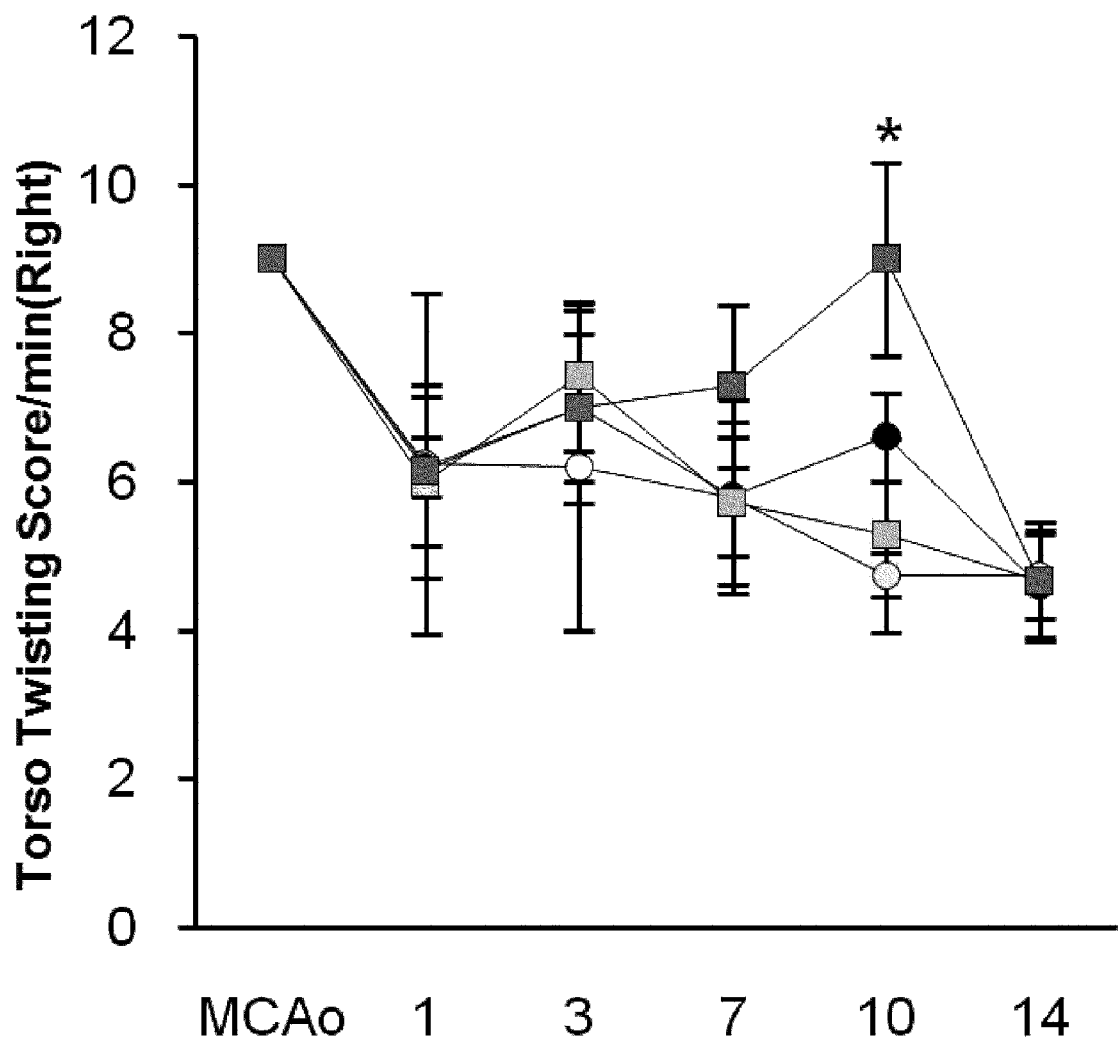
Figure 6D:
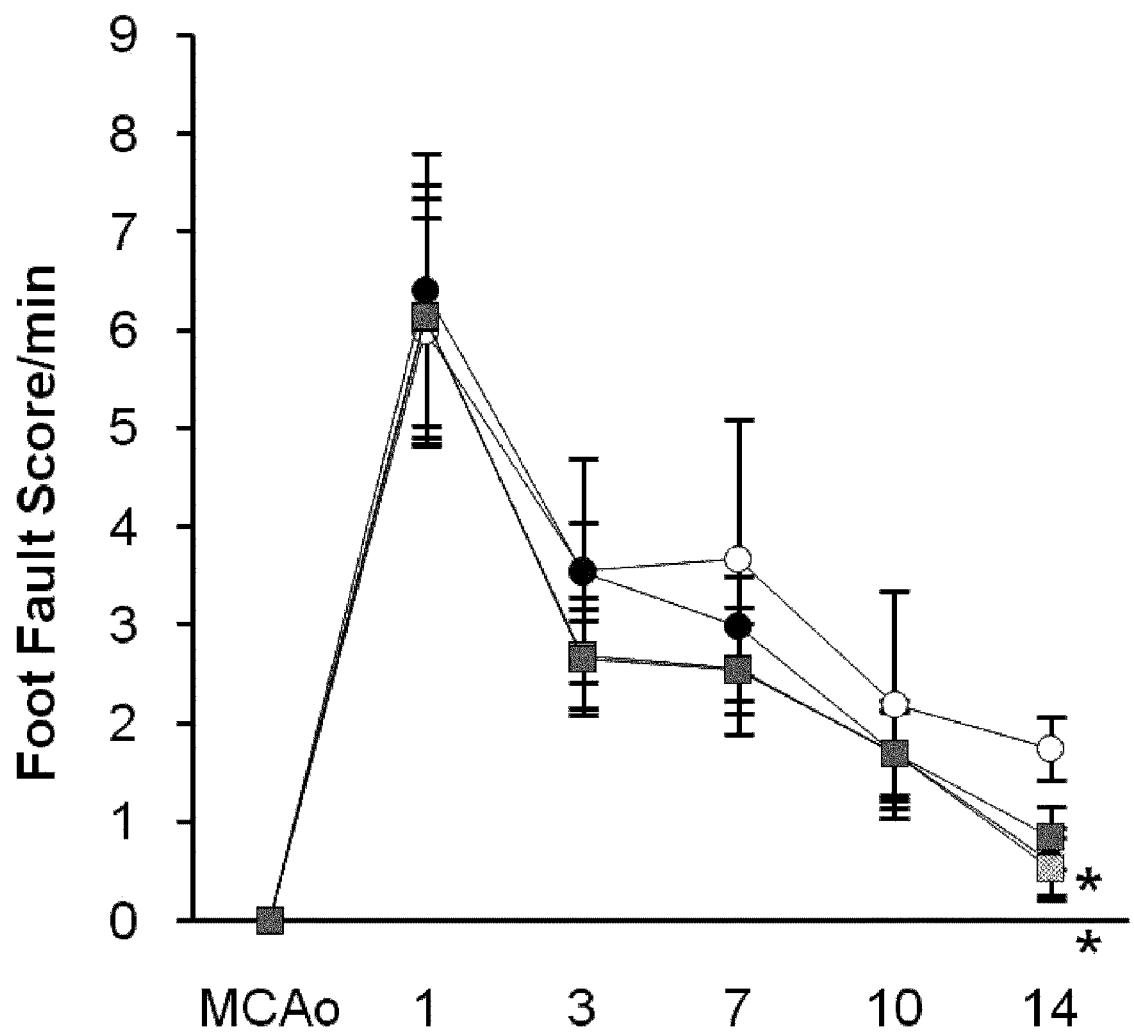
Figure 6E:
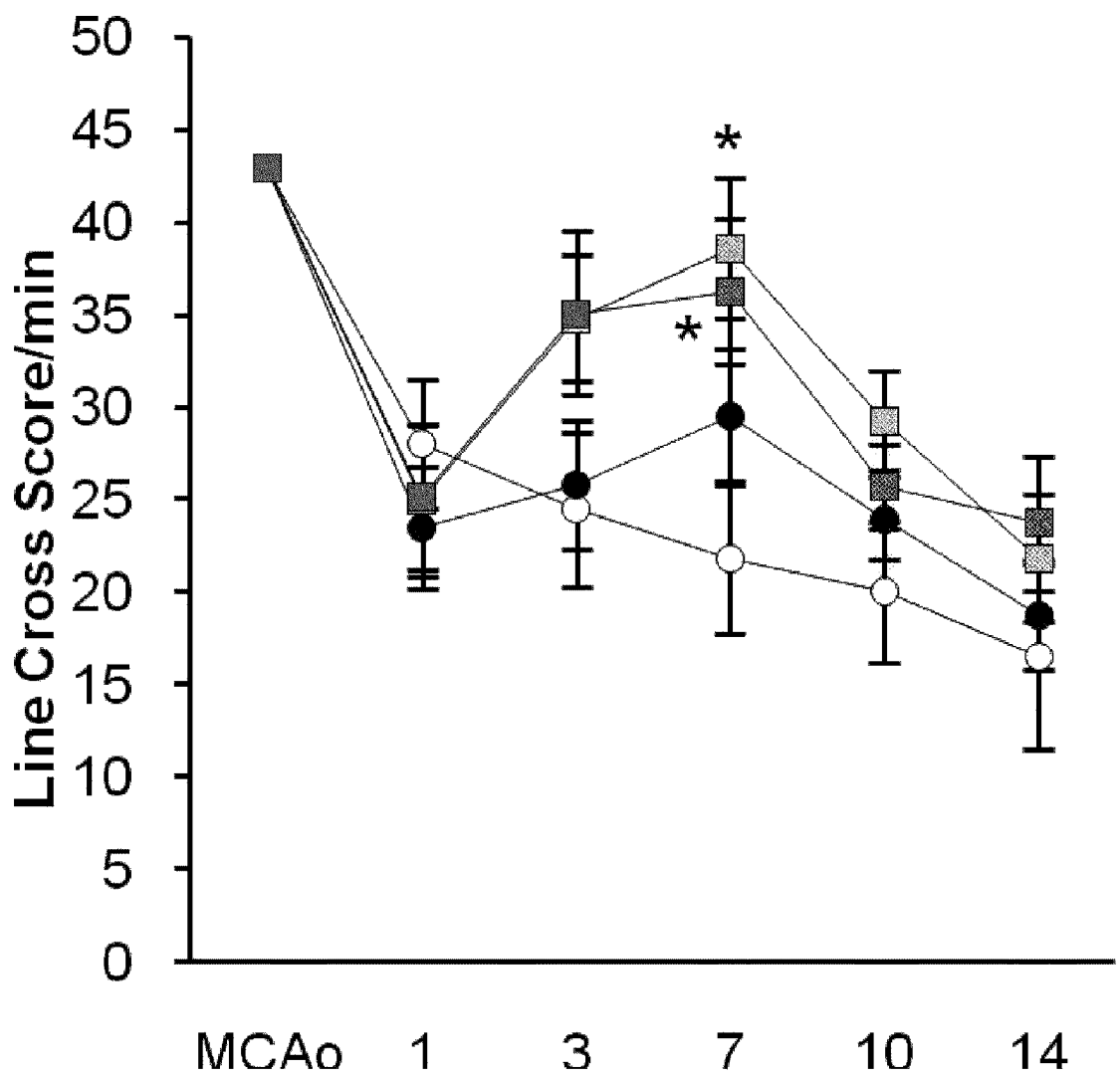
Figure 6F:
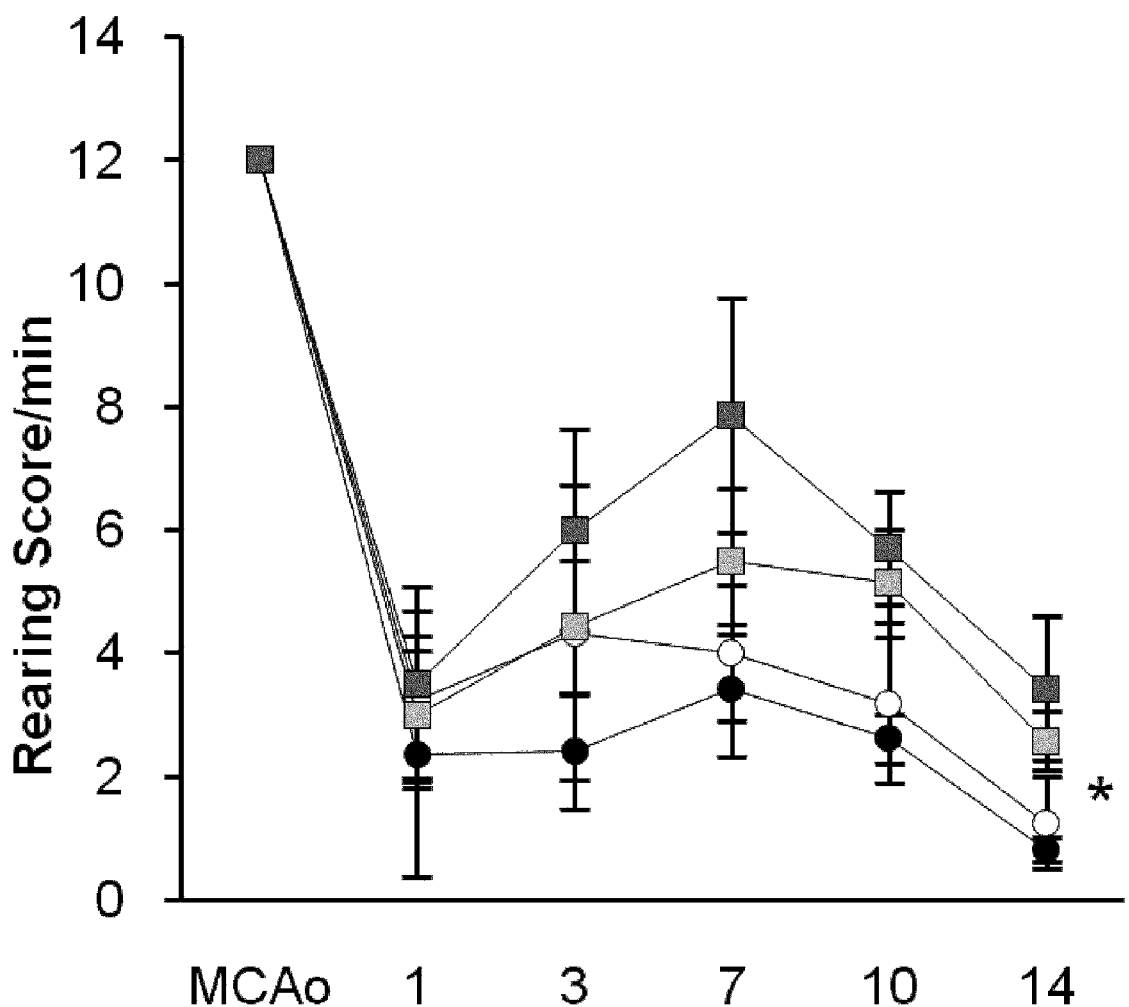
Figure 6G:
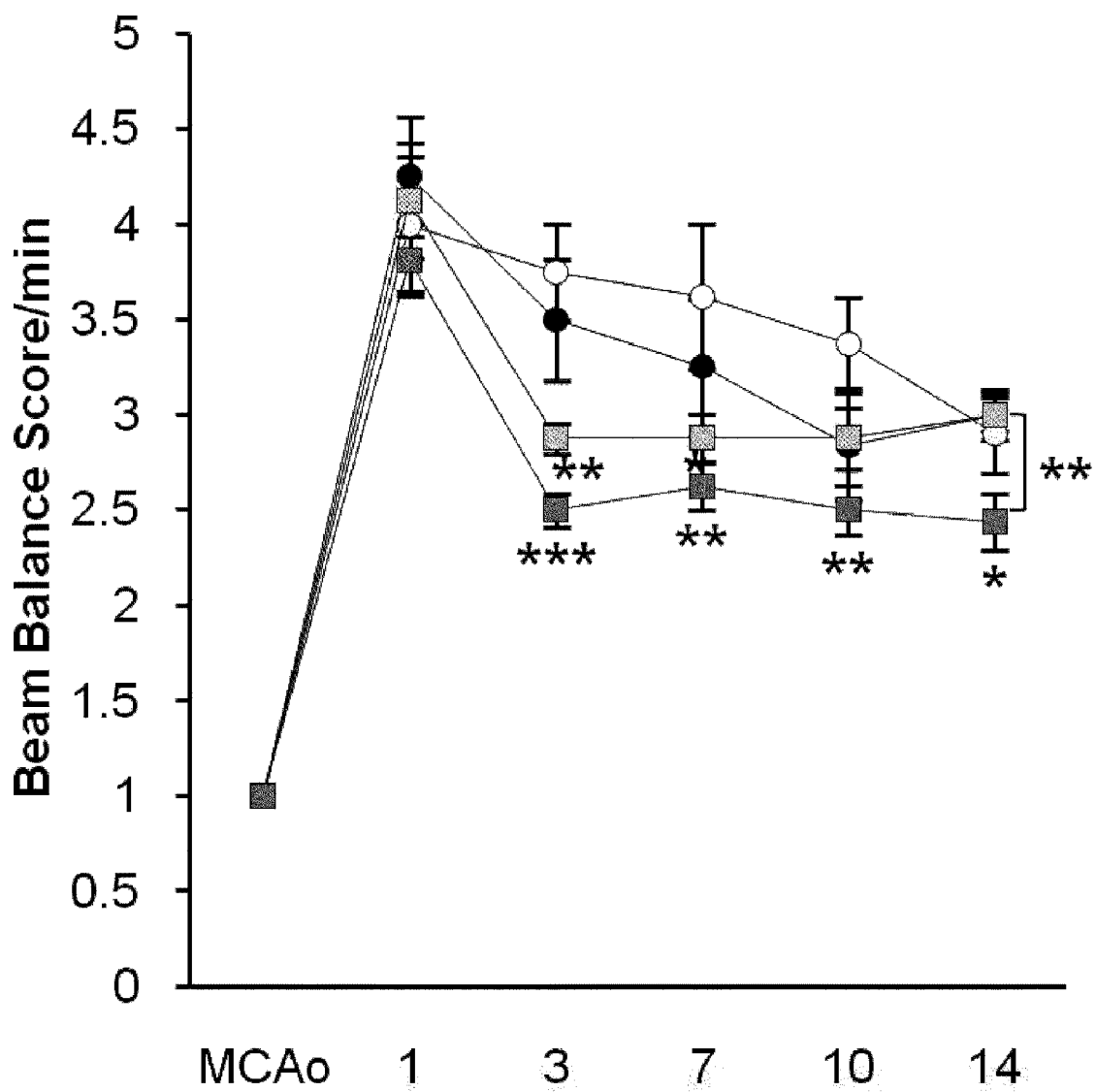
Figure 6H:
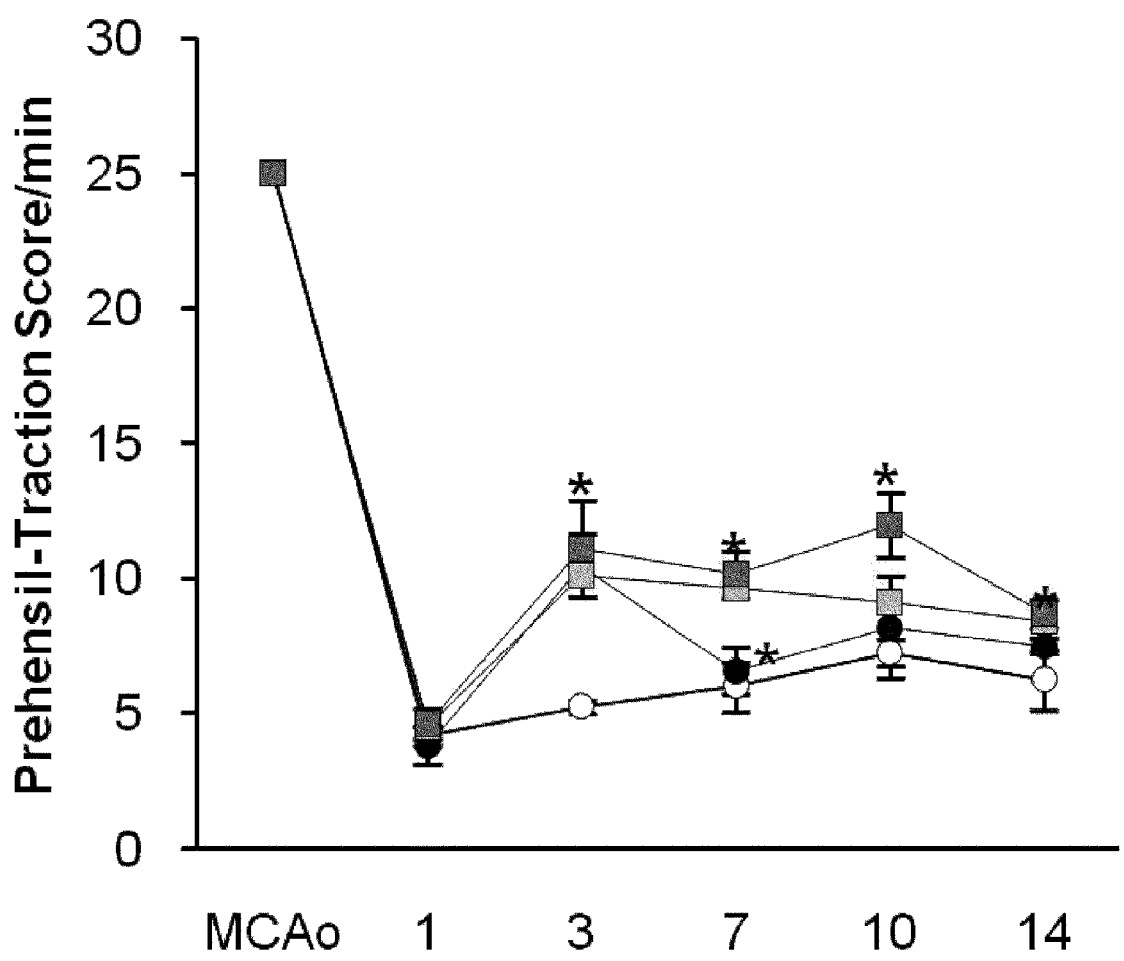
Figure 6I:
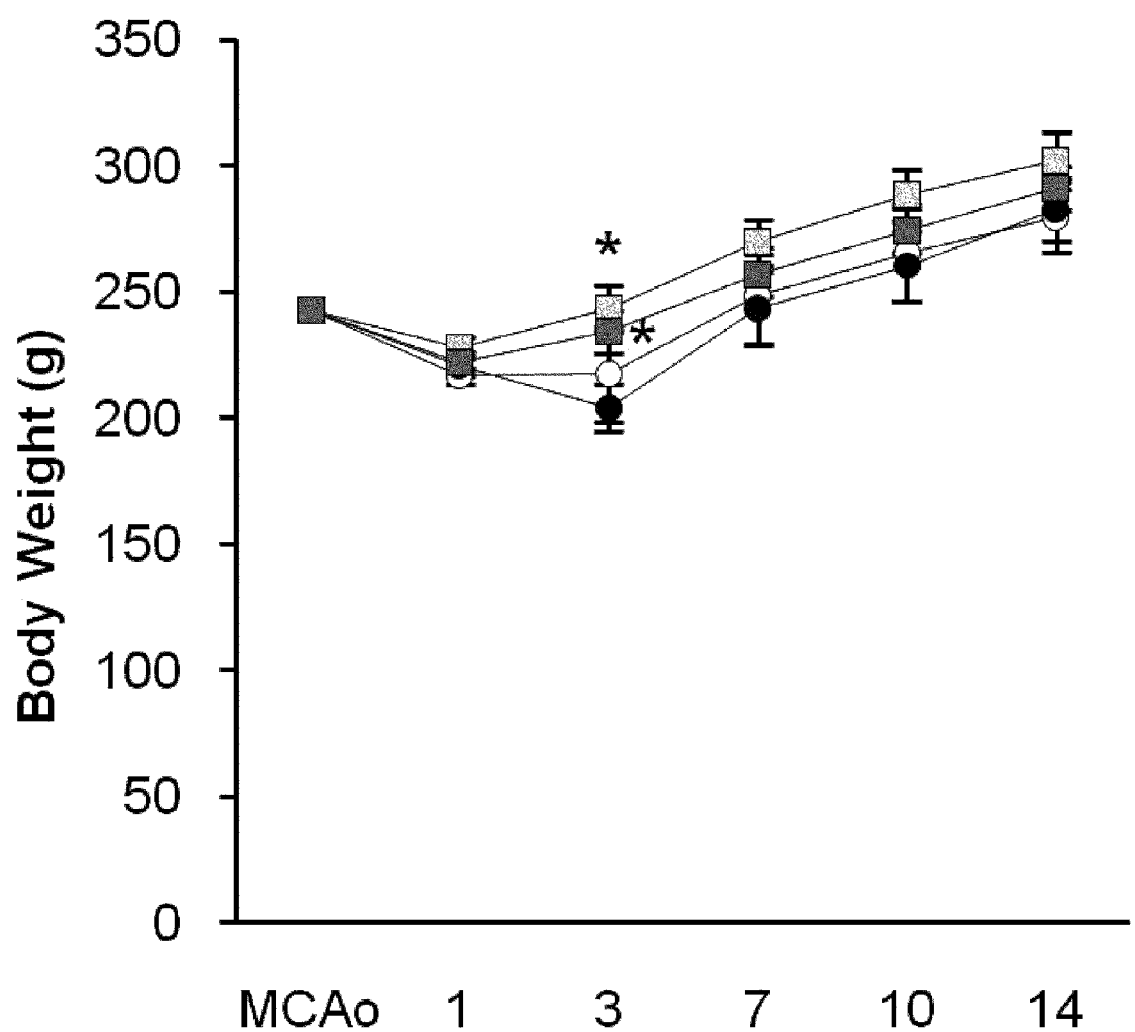

The secretome single-dose administration group and the secretome multiple-dose administration group showed significant improvement on day 3 of treatment compared with the PBS control group (FIG. 6i). However, the body weight difference between groups lost statistical significance with the passage of time.

Behavior Analysis

In the torso twisting test, the secretome multiple-dose treatment group induced a statistically significant improvement effect in the asymmetric movement of the left torso, which corresponds to the brain injury site, when compared with the other groups (FIG. 6b). Whereas, a statistical significance was not observed in the asymmetric movement of the right torso, which corresponds to the non-injury site, except for day 10 in the multiple-dose administration group of the secretome (FIG. 6c).

The repeated administration of the secretome showed a tendency to reduce the foot fault frequency in a net, but a statistic significance from the control group was not shown except for day 14 (FIG. 6d). The single-dose administration and the multiple-dose administration of the secretome also showed an improvement trend in the line cross, which measures behavioral activeness per unit time (FIG. 6e).

The single-dose administration and the multiple-dose administration of the secretome were confirmed to have a tendency to induce an improvement in the rearing score when compared with the other experimental groups (FIG. 6f). The multiple-dose administration of the secretome showed a statistically significant behavior improvement effect in the beam balance test when compared with the two control groups, and this effect was shown from day 3 of treatment, indicating an immediate effect (FIG. 6g). In addition, the multiple-dose administration of the secretome showed a statistically significant effect in the prehensile traction test on day 7 of treatment (injection) when compared with the two control groups (FIG. 6h).

Modified Neurological Severity Score (mNSS) Analysis

As shown in FIG. 6a, in the analysis of mNSS, the secretome multiple-dose treatment group showed a significantly higher treatment effect (behavior improvement) from the early treatment when compared with the PBS control and the medium control. The secretome single-does treatment group also exerted a significant treatment effect when compared with the control groups during the experimental period, and showed a superior behavior improvement effect when compared with the medium control group.

Ischemic Lesion Site Analysis

Figure 7:
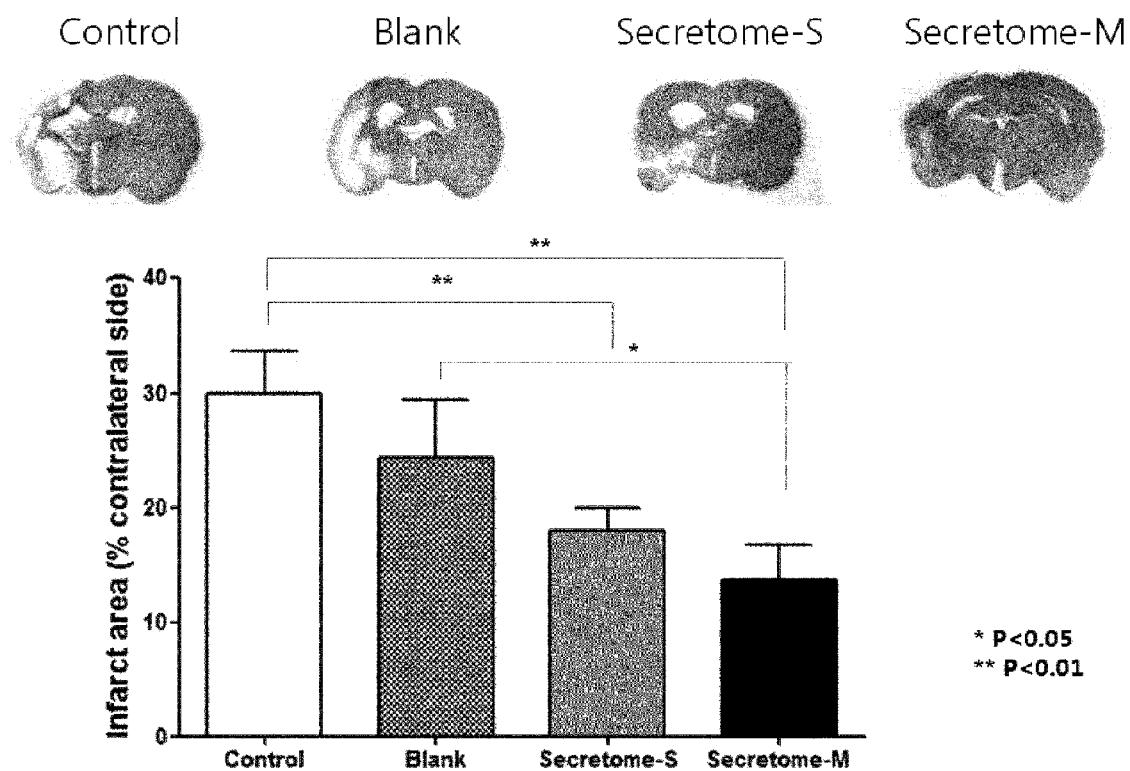
FIG. 7 shows the sizes of an ischemic lesion site in a PBS control group, a medium control group, a secretome single-dose treatment group (Secretome-S), and a secretome multiple-dose treatment group (Secretome-M).

FIG. 7 shows the effect of the neural precursor cell (NPC)-derived secretome on the infarction size 14 days after administration in the rat pMCAo model. Representative images after 14 days of treatment in rats administered with PBS (Control), medium (Blank), NPC-derived secretome single-dose (Secretome-S), or NPC-derived secretome repeated administration (Secretome-M) are shown. The effect of the neural precursor cell-derived secretome on the infarction size after 14 days in the rat pMCAo model is shown. *$P<0.01$ for single-dose administration and multiple-dose administration compared with PBS group. Especially, it was confirmed that the multiple-dose administration had a significant improvement effect of $P<0.05$ compared with the medium control group (blank).

Anti-Inflammatory Effect—ED-1 Positive Cell Reduction

Figure 8A:
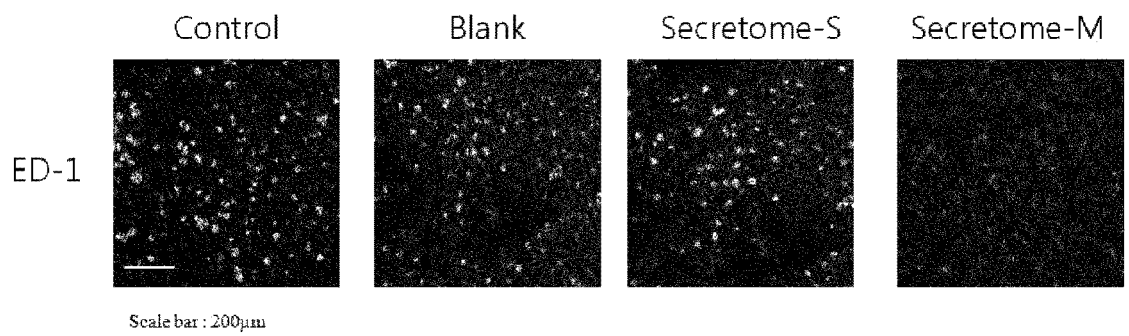
FIGS. 8a to 8b show that the repeated administration of the neural precursor cell (NPC)-derived secretome (Secretome-M) induced a significant reduction in the number of ED-1 positive cells. Scale bar: 200 μm, *P<0.001.
Figure 8B:
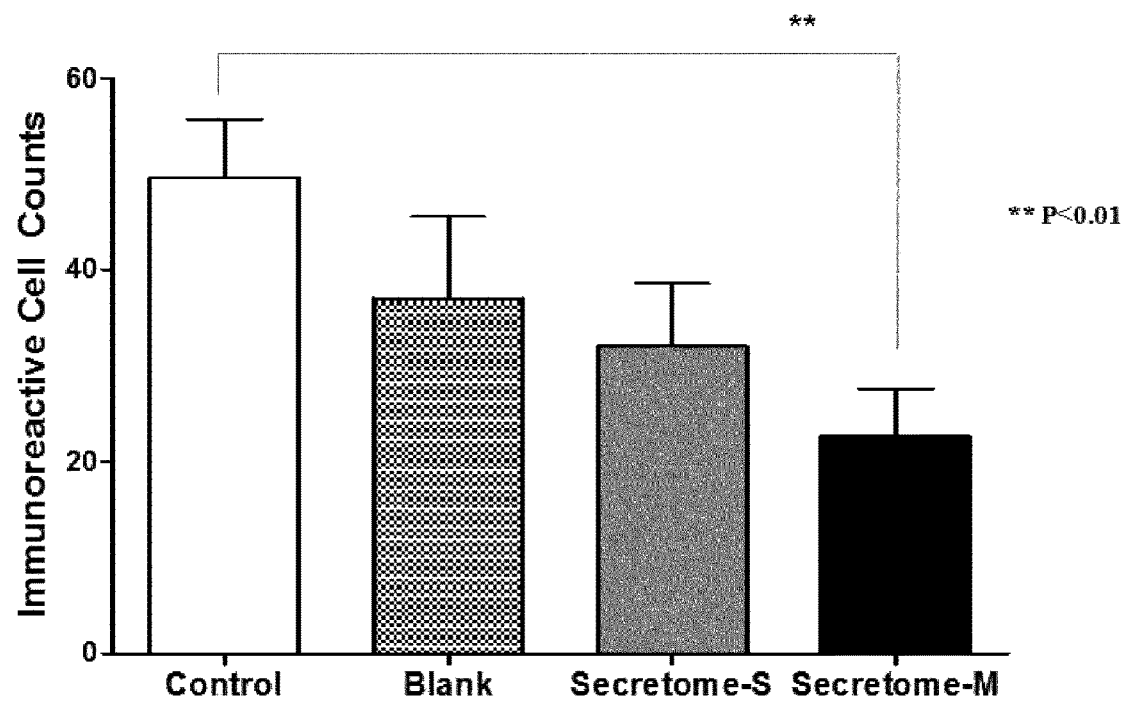
Figure 9A:
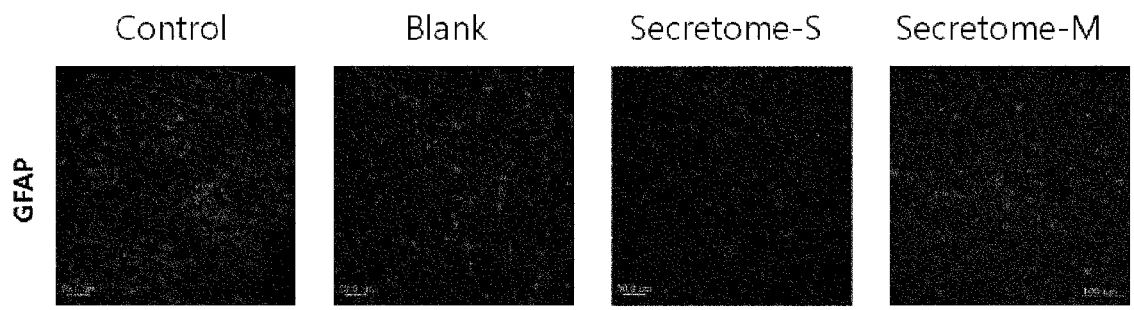
FIGS. 9a to 9b show that the repeated administration of the neural precursor cell (NPC)-derived secretome (Secretome-M) induced a significant reduction in the number of GFAP positive cells. Scale bar: 200 μm, *P<0.05 및 ***P<0.001.
Figure 9B:
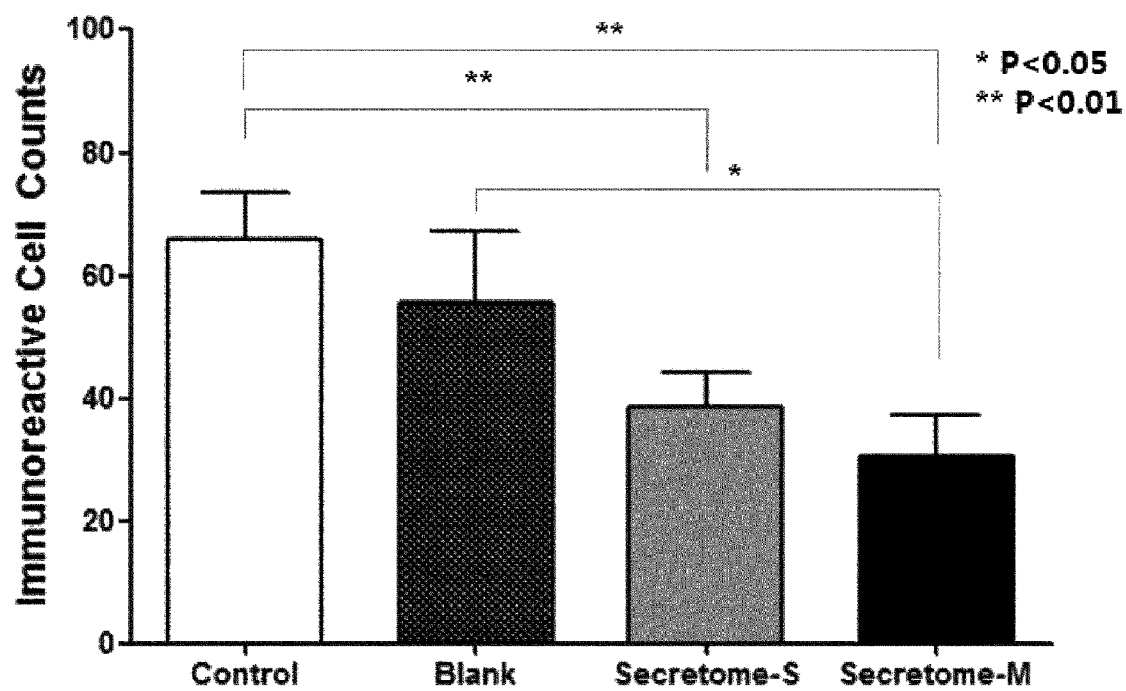

FIGS. 8a-8b show that the treatment with the NPC-derived secretome reduced the frequency of ED-1 positive cells in the ipsilateral striatum, and the repeated administration of secretome significantly induced the reduction of ED-1 positive cells. Scale bar: 200 μm. The number of ED-1 positive cells was measured in at least five separate microscopic regions. Measurement values are mean±S.E.M. *P<0.001 when compared between the control group and the secretome-repeated administration group Anti-Inflammatory Effect—GFAP Positive Cell Reduction FIGS. 9a-9b show that the treatment with the NPC-derived secretome reduced the frequency of GFAP positive cells in the ipsilateral striatum, and the repeated administration of the secretome significantly induced the reduction of GFAP positive cells. Especially, the expression of GFAP also induced a significant reduction in the secretome repeated treatment group compared with the medium control group (Blank). Scale bar: 200 μm. The number of GFAP positive cells was measured in at least five separate microscopic regions. The measurement values are mean±S.E.M. *P<0.05 and ***P<0.001 when the multiple comparisons were made among the groups.

Mobilization Effect of Endogenous Stem Cells

Figure 10:
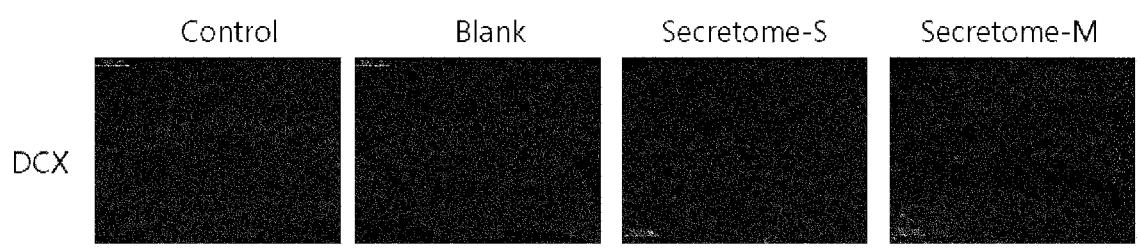
FIG. 10 shows the mobilization of endogenous neural stem cells in rat brain tissues due to the repeated administration of neural precursor cell (NPC)-derived secretome (Secretome-M). Scale bar: 500 μm.

FIG. 10 shows the mobilization of endogenous neural stem cells due to the administration of the secretome in rat brain tissues. Testing was carried out after 14 days of administration of the secretome. DCX (red) positive cells were observed in the rat ischemic brain. Scale bar: 500 μm.

New Vessel Increase Effect

Figure 11:
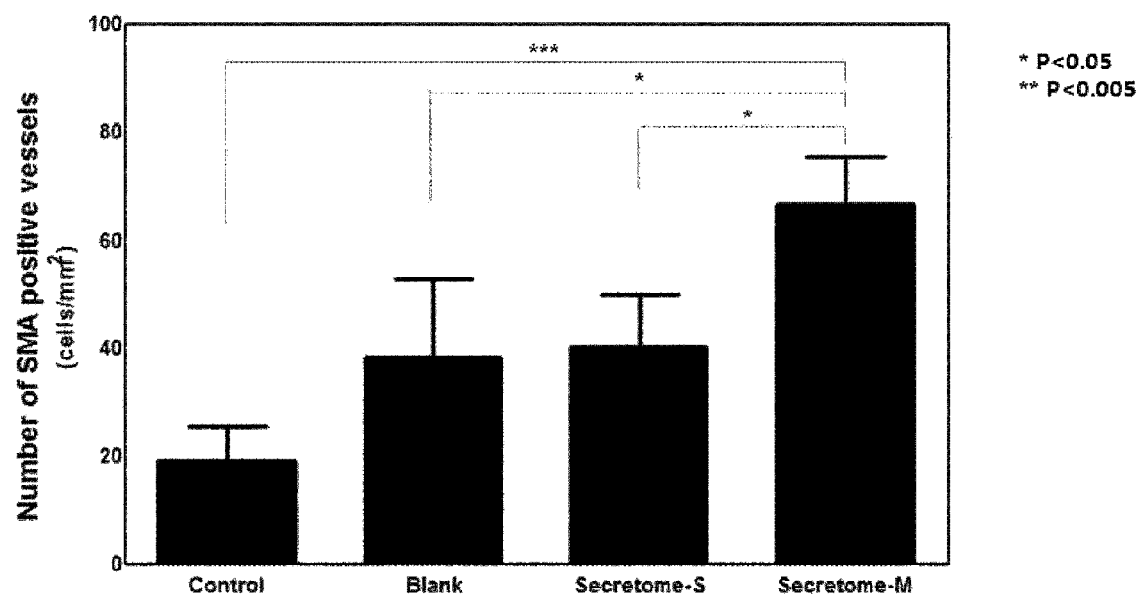
FIG. 11 shows that the repeated administration of the neural precursor cell (NPC)-derived secretome significantly reduced the number of α-SMA positive vessels. *P<0.005.

FIG. 11 shows that the treatment with the NPC-derived secretome reduced the frequency of α-SMA positive vessels in the ipsilateral striatum, and the repeated administration of secretome significantly increased the number of vessels. The number of α-SMA positive vessels was measured in at least five separate microscopic regions. Measurement values are mean±S.E.M. *P<0.005 when compared between the control group and the secretome-repeated administration (Secretome-M) group.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating ischemic cerebrovascular disease, ischemic heart disease, myocardial infarction, Alzheimer's disease, Parkinson's disease, Lewy body disease, multiple sclerosis, amyotrophic lateral sclerosis, or spinal cord injury, the method comprising administering, to a subject, a composition comprising: (a) a therapeutically effective amount of a secretome derived from poly-sialylated neural cell adhesion molecule (PSA-NCAM)-positive neural precursor cells (NPCs); and (b) a pharmaceutically acceptable carrier, wherein the secretome is in a form of a cell conditioned medium obtained by culturing neural precursor cells in a cell culture medium and then removing the cells.

2. The method of claim 1, wherein the neural precursor cells are differentiated from pluripotent stem cells.

3. The method of claim 2, wherein the pluripotent stem cells are embryonic stem cells, induced pluripotent stem cells (iPSCs), embryonic germ cells, or embryonic carcinoma cells.

4. The method of claim 1, wherein the neural precursor cells are neural precursor cells before or after a stage of neural rosettes differentiated from pluripotent stem cells.

5. The method of claim 1, wherein the cell conditioned medium is obtained by culturing the neural precursor cells in a serum-free cell culture medium comprising insulin/transferrin/selenium (ITS) and basic fibroblast growth factor (bFGF) and then removing the cells.

6. The method of claim 1, wherein the secretome comprises the following proteins: agrin, annexin A5, basigin (BSG), biglycan, calponin-3), coactosin-like protein, cofilin-1, collagen alpha-2, cullin-3, destrin, dystroglycan, ephrin-B2, exportin-2, ezrin, fibronectin, fibulin-1, frizzled-related protein, galectin-3 binding protein, granulins, growth/differentiation factor 11, haptoglobin, hemopexin, high mobility group protein B2, hornerin, importin-9, insulin-like growth factor-binding protein 2, lupus La protein, macrophage migration inhibitory factor, midkine, moesin, neuropilin 2, pleiotrophin, profilin-1, protein DJ-1, radixin, secreted frizzled-related protein-2, septin-11, talin-1, testican, thymopoietin, transgelin-3, and vimentin.

7. The method of claim 1, wherein the secretome comprises the following proteins: agrin, annexin A2, attractin, biglycan, ceruloplasmin, cofilin-1, collagen alpha-1, coronin-1X, dermicidin, DERP12, ephrin-B3, exostosin-2, ezrin, galectin-3 binding protein, granulins, growth/differentiation factor 11, haptoglobin, hemopexin, high mobility group protein B2, hornerin, insulin-like growth factor-binding protein 2, lupus La protein, midkine, moesin, multiple epidermal growth factor-like domains protein 8, nidogen-1, parathymosin, profilin-2, protein DJ-1, secreted frizzled-related protein-2, secretogranin, talin-1, thymosin beta-4, transforming growth factor-beta-induced protein ig-h3 (TGFBI), transgelin, and vimentin.

8. The method of claim 1, wherein the ischemic cerebrovascular disease is ischemic stroke.

9. The method of claim 1, wherein the composition is formulated for single-dose administration.

10. The method of claim 1, wherein the composition is formulated for multi-dose administration.

11. The method of claim 1, the PSA-NCAM-positive neural precursor cells are separated from neural rosettes, which are differentiated from pluripotent stem cells, using an anti-PSA-NCAM-antibody.

* * * * *